United States Patent [19]

Hess et al.

[11] 4,080,368

[45] Mar. 21, 1978

[54] FURYL-2-OXO-ALKANEPHOSPHONATES

[75] Inventors: Hans-Jurgen E. Hess, Old Lyme; Michael R. Johnson, Gales Ferry; Jasjit S. Bindra, Groton; Thomas K. Schaaf, Old Lyme, all of Conn.

[73] Assignee: Pfizer Inc., New York, N.Y.

[21] Appl. No.: 789,519

[22] Filed: Apr. 21, 1977

Related U.S. Application Data

[60] Division of Ser. No. 705,768, Jul. 15, 1976, which is a division of Ser. No. 633,374, Nov. 19, 1975, Pat. No. 3,980,642, which is a division of Ser. No. 485,596, Jul. 3, 1974, Pat. No. 3,956,284, which is a continuation-in-part of Ser. No. 425,517, Dec. 17, 1973, abandoned, which is a continuation-in-part of Ser. No. 271,220, Jul. 13, 1972, abandoned.

[51] Int. Cl.$^2$ .............................................. C07F 9/40
[52] U.S. Cl. .................................................. 260/347.8
[58] Field of Search .................................... 260/347.8

[56] References Cited

PUBLICATIONS

Pudovik, Chemical Abstracts, vol. 45, (1951).

*Primary Examiner*—Richard L. Raymond
*Attorney, Agent, or Firm*—Connolly and Hutz

[57] ABSTRACT

The 15-substituted-ω-pentanorprostaglandins and various intermediates employed in their preparation. The novel prostaglandins of this invention have been found to have activity profiles comparable to the parent prostaglandins, but exhibit a greater tissue specificity of action.

2 Claims, No Drawings

FURYL-2-OXO-ALKANEPHOSPHONATES

CROSS REFERENCE TO RELATED APPLICATIONS

This application is a division of application Ser. No. 705,768 filed July 15, 1976 which, in turn, is a division of application Ser. No. 633,374 filed Nov. 19, 1975 and now U.S. Pat. No. 3,980,642, which, in turn, is a division of application Ser. No. 485,596 filed July 3, 1974 and now U.S. Pat. No. 3,956,284, which, in turn, is a continuation-in-part of application Ser. No. 425,517 filed Dec. 17, 1973 and now abandoned, which, in turn, is a continuation-in-part of application Ser. No. 271,220 filed July 13, 1972 and now abandoned.

BACKGROUND OF THE INVENTION

This invention relates to certain novel analogs of the naturally occurring prostaglandins. In particular, it relates to novel 15-substituted-ω-pentanorprostaglandins and various novel intermediates useful in their preparation.

The prostaglandins are C-20 unsaturated fatty acids which exhibit diverse physiological effects. For instance, the prostaglandins of the E and A series are potent vasodilators (Bergstrom, et al., *Acta Physiol. Scand.* 64:332-33 1965 and Bergstrom, et al., *Life Sci.* 6:449-455, 1967) and lower systemic arterial blood pressure (vasodepression) on intravenous administration (Weeks and King, *Federation Proc.* 23:327, 1964; Bergstrom, et al., 1965; op. cit.; Carlson, et al., *Acta Med. Scand.* 183:423-430, 1968; and Carlson, et al., *Acta Physiol. Scand.* 75:161-169, 1969). Another well known physiological action for $PGE_1$ and $PGE_2$ is as a bronchodilator (Cuthbert, *Brit. Med. J.* 4:723-726, 1969).

Still another important physiological role for the natural prostaglandins is in connection with the reproductive cycle. $PGE_2$ is known to possess the ability to induce labor (Karim, et al., *J. Obstet. Gynaec. Brit. Cwlth.* 77:200-210, 1970), to induce therapeutic abortion (Bygdeman, et al., *Contraception*, 4, 293 (1971) and to be useful for control of fertility (Karim, *Contraception*, 3, 173 (1971)). Patents have been obtained for several prostaglandins of the E and F series as inducers of labor in mammals (Belgian Pat. No. 754,158 and West German Pat. No. 2,034,641), and on $PGF_1$, $F_2$, and $F_3$ for control of the reproductive cycle (South African Pat. No. 69/6089). It has been shown that luteolysis can take place as a result of administration of $PGE_{2\alpha}$[Labhsetwar, *Nature* 230 528 (1971)] and hence prostaglandins have utility for fertility control by a process in which smooth muscle stimulation is not necessary.

Still other known physiological activities for $PGE_1$ are in the inhibition of gastric acid secretion (Shaw and Ramwell, In: *Worcester Symp. on Prostaglandins*, New York, Wiley, 1968, p. 55-64) and also of platelet aggregation (Emmons, et al., *Brit. Med. J.* 2:468-472, 1967).

It is now known that such physiological effects will be produced in vivo for only a short period, following the administration of a prostaglandin. A substantial body of evidence indicates that the reason for this rapid cessation of activity is that the natural prostaglandins are quickly and efficiently metabolically deactivated by β-oxidation of the carboxylic acid side-chain and by oxidation of the 15α-hydroxyl group (Anggard, et al., *Acta. Physiol. Scand.*, 81, 396 (1971) and references cited therein). It has been shown that placing a 15-alkyl group in the prostaglandins has the effect of increasing the duration of action possibly by preventing the oxidation of the C15-hydroxyl [Yankee and Bundy, JACS 94, 3651 (1972)], Kirton and Forbes, *Prostaglandins*, 1, 319 (1972).

It was, of course, considered desirable to create analogs of the prostaglandins which would have physiological activities equivalent to the natural compounds, but in which the selectivity of action and the duration of the activity would be increased. Increased selectivity of action would be expected to alleviate the severe side effects, particularly gastrointestinal side effects, frequently observed following systemic administration of the natural prostaglandins (*Lancet*, 536, 1971).

SUMMARY OF THE INVENTION

These needs are met by the novel compounds of this invention, the 15-substituted-ω-pentanorprostaglandins in which the substituent in question is of the structure:

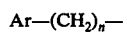

$$Ar-(CH_2)_n-$$

wherein Ar is α- or β-furyl; or α- or β-thienyl; and n is an integer from 0 to 5, with the proviso that when n = 0 said prostaglandin is a 13,14 dihydro prostaglandin, and in which the remaining 15-hydrogen may be replaced by a 15-lower alkyl group if desired.

In addition to the 15-substituted-ω-pentanorprostaglandins wherein the prostaglandin is $PGF_{1\alpha}$, $PGF_{1\beta}$, $PGE_1$, $PGA_1$; 13, 14-dihydro $PGF_{1\alpha}$, $PGF_{1\beta}$, $PGE_1$, and $PGA_1$; $PGF_{2\alpha}$, $PGF_{2\beta}$, $PGE_2$, $PGA_2$; 13,14-dihydro $PGF_{2\alpha}$, $PGF_{2\beta}$, $PGE_2$, and $PGA_2$; 15-lower alkyl derivatives of the above compounds, this invention further comprises a compound of the structure:

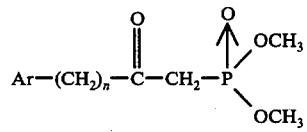

wherein Ar is α- or β-furyl; α- or β-thienyl; and n is an integer from 0 to 5, a useful reagent for preparation of the novel prostaglandins; and useful intermediates for these prostaglandins as follows:

a compound of the structure:

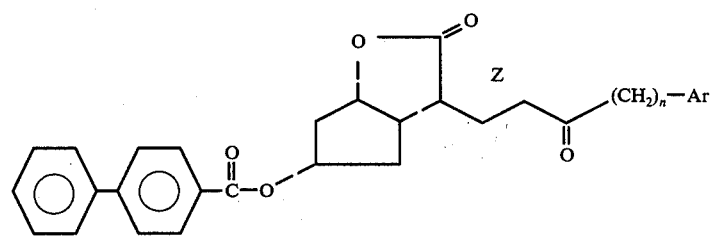

a compound of the structure:

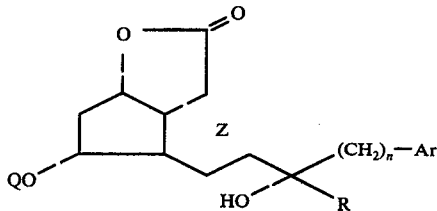

wherein R is hydrogen or lower alkyl; and Q is hydrogen or parabiphenylcarbonyl;

a compound of the structure:

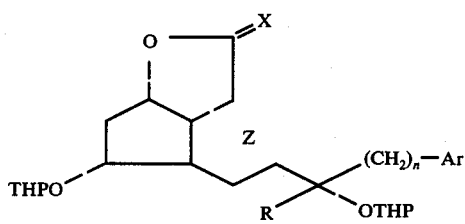

wherein THP is tetrahydropyranyl, $n$ is an integer from 0 to 5; Z is a single bond or a trans double bond with the proviso that when $n$ is 0, Z is a single bond, and X is $=O$ or

a compound of the structure:

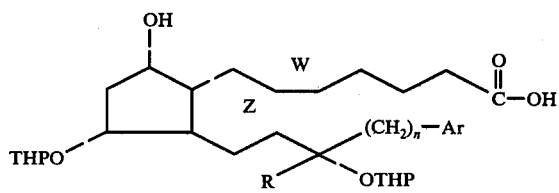

wherein w is a single bond or a cis double bond and Z, THP, R, Ar and $n$ are as previously defined;

a compound of the structure:

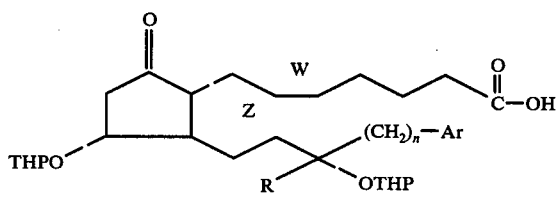

wherein W, Z, THP, R, Ar and $n$ are as previously defined, and especially 16-α-thienyl-ω-tetranor $PGE_2$; 16-α-thienyl-ω-tetranor $PGE_1$; 16-β-thienyl-ω-tetranor $PGE_2$; 17-α-thienyl-ω-trisnor $PGE_2$; 17-α-furyl-ω-trisnor $PGE_2$; 17-α-furyl-ω-trisnor $PGF_{2\alpha}$ and 17-α-thienyl-ω-trisnor $PGE_{2\alpha}$ 17-β-furyl-ω-trisnor $PGE_2$; 17-β-furyl-ω-trisnor $PGF_{2\alpha}$; 17-β-thienyl-ω-trisnor $PGF_{2\alpha}$; 17-β-thienyl-ω-trisnor $PGE_2$ and the $C_{15}$ epimers of these compounds.

It will be understood by those skilled in the art that in structures depicting hemiacetals, no sterochemistry is implied at the lactol carbon.

It will be further understood that as herein used, the expression "prostaglandin of the 'zero' series," for example $PGE_0$, refers to prostaglandin in which the 5–6 and 13–14 double bonds have been saturated; i.e.: $PGE_0$ is 5–6, 13–14, tetrahydro $PGE_2$. In addition, the phrases "zero series", "one series" or "two series" as herein employed refer to the degree of unsaturation in the side chains, e.g. $PGE_2$, $PGA_2$, $PGF_{2\alpha}$, and $PGF_{2\beta}$ are prostaglandins of the "two series" whereas $PGE_1$, $PGF_{1\alpha}$, $PGF_{1\beta}$ and $PGA_1$ are prostaglandins of the "one series". Furthermore, as herein employed the phrase lower "alkyl group" refers to alkyl groups containing from 1 to 4 carbon atoms.

DETAILED DESCRIPTION OF THE INVENTION

As shown in Scheme A, the first step (1→2) is the condensation of the appropriate ester with a dialkyl methylphosphonate to produce ketophosphonate 2. Typically, the desired methyl ester is condensed with dimethyl methyl phosphonate.

In 2→3 the ketophosphonate 2 is caused to react with the known [Corey et al., J. Org. Chem. 37, 3043 (1972)] aldehyde H to produce, after chromatography or crystallization, the enone 3.

The enone 3 can be converted to a mixture of tertiary alcohols 13 and 14 by reaction with the appropriate lithium alkyl or grignard reagent and the isomeric 13 and 14 can be separated by column or high pressure liquid chromatography. The enone 3 can be reduced with zinc borohydride to a mixture of alcohols, 4 and 5 which can be separated as above. Lithium triethyl borohydride is especially preferred when 1-2 reduction is desired. In this reaction ethers such as tetrahydrofuran or 1,2 dimethoxy ethane are usually employed as solvents.

Further transformations of 4 are shown on Scheme B.:

4→6 is a base catalyzed transesterification in which the p-biphenyl-carbonyl protecting group is removed. This is most conveniently conducted with potassium carbonate in methanol or methanol-tetrahydrofuran solvent. 6→7 involves the protection of the two free hydroxyl groups with an acid-labile protecting group. Any sufficiently acid labile group is satisfactory; however, the most usual one is tetrahydropyranyl, which can be incorporated in the molecule by treatment with dihydropyran and an acid catalyst in an anhydrous medium. The catalyst is usually p-toluenesulfonic acid.

Scheme A

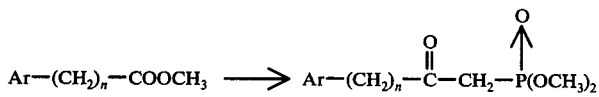

1          2

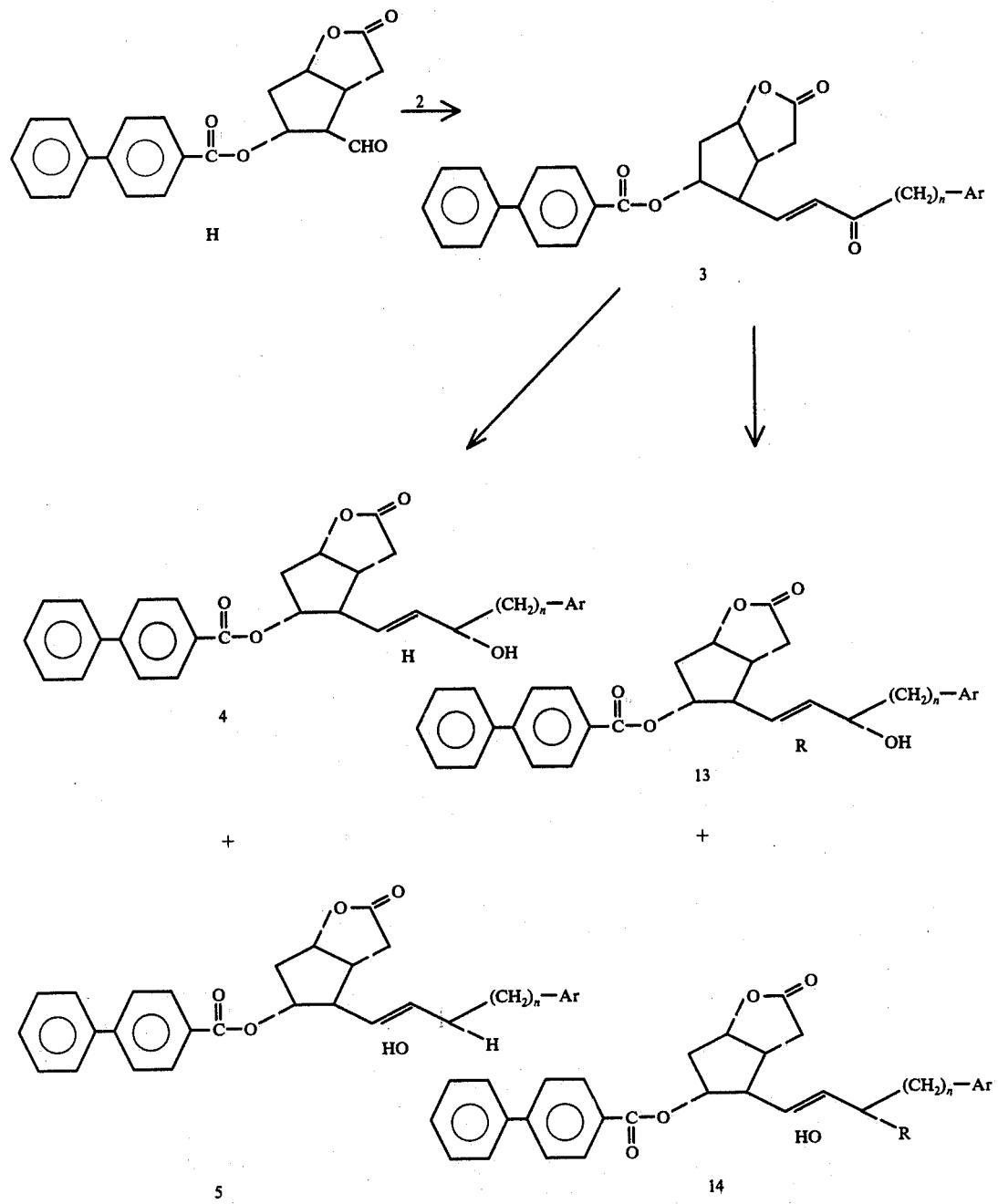
Scheme B
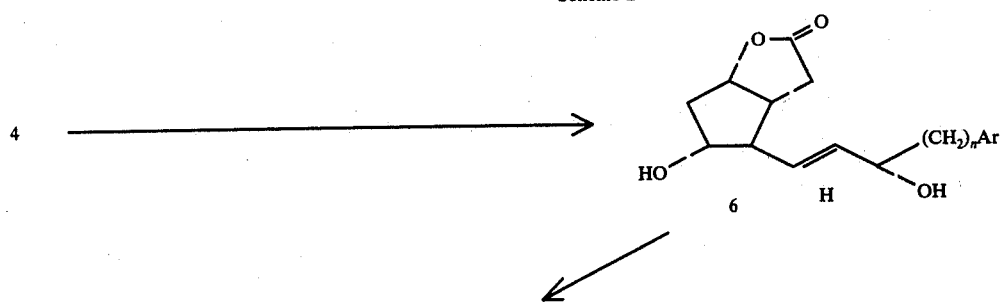

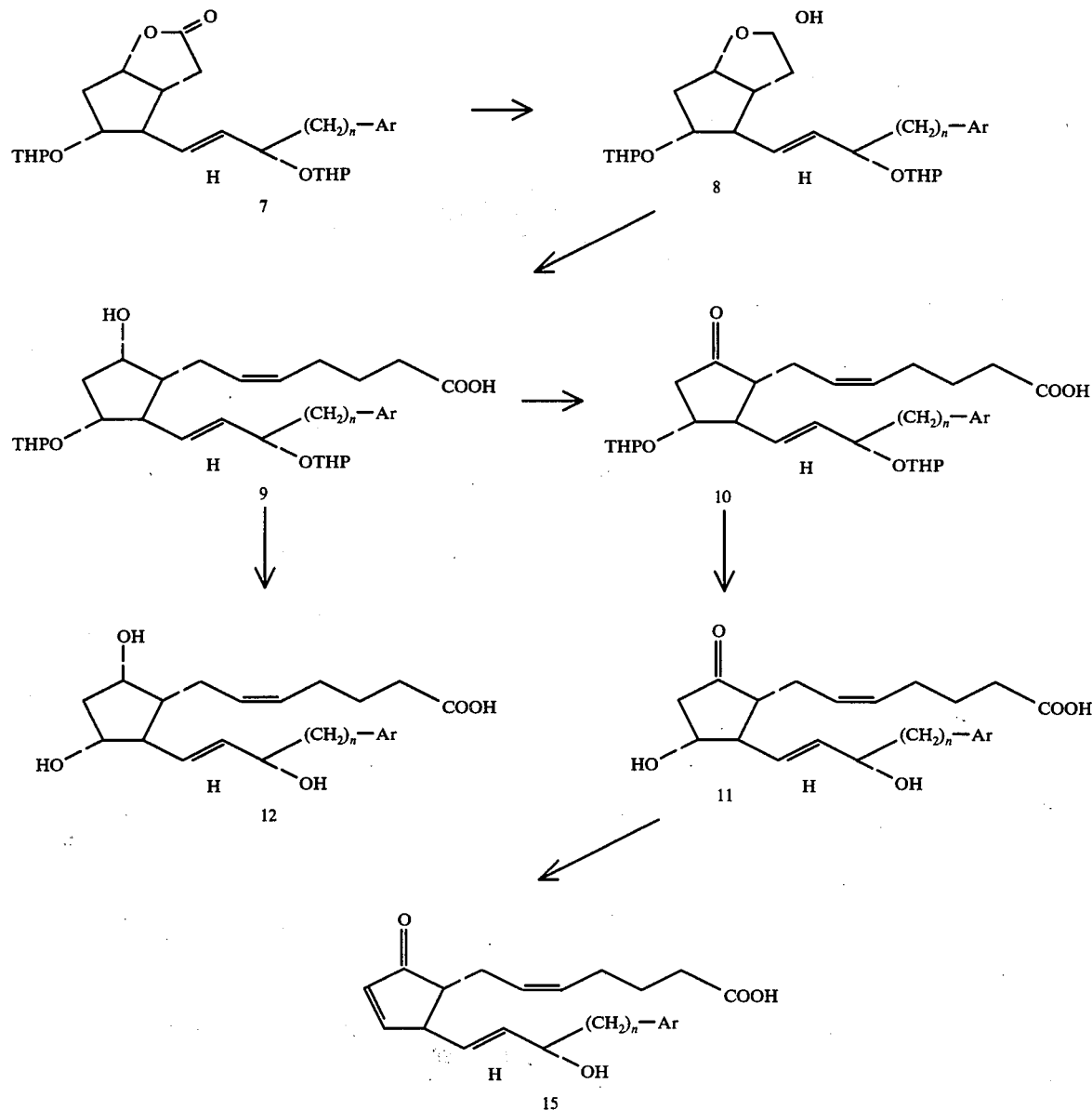

7→8 is a reduction of the lactone 7 to the hemiacetal 8 using diisobutyl aluminum hydride in an inert solvent. Low reaction temperatures are preferred and −60° to −70° C are usual. However, higher temperature may be employed if over-reduction does not occur. 8 is purified, if desired, by column chromatography.

8→9 is a Wittig condensation in which hemiacetal 8 is reacted with (4-carbohydroxy-n-butyl)triphenylphosphonium bromide in dimethyl sulfoxide, in the presence of sodium methylsulfinyl methide. 9 is purified as above.

The conversion 9→12 is an acidic hydrolysis of the tetrahydropyranyl groups. Any acid may be used which does not cause destruction of the molecule in the course of the removal of the protecting group; however, this is accomplished most often by use of 65% aqueous acetic acid. The product is purified as above.

9→10 is an oxidation of the secondary alcohol 9 to the ketone 10. This may be accomplished using any oxidizing agent which does not attack double bonds; however, the Jones reagent is usually preferred. The product is purified as above.

10→11 is carried out in the same manner as 9→12. The product is purified as above.

11→15 is an acid-catalyzed dehydration. Any acid may be used for the process which does not cause extensive descomposition of the product, but the most usual procedure consists of dissolving 11 in an excess of 97% formic acid followed by dilution with ice water and extraction of the product after the starting material has been consumed. The product is purified as above.

Scheme C
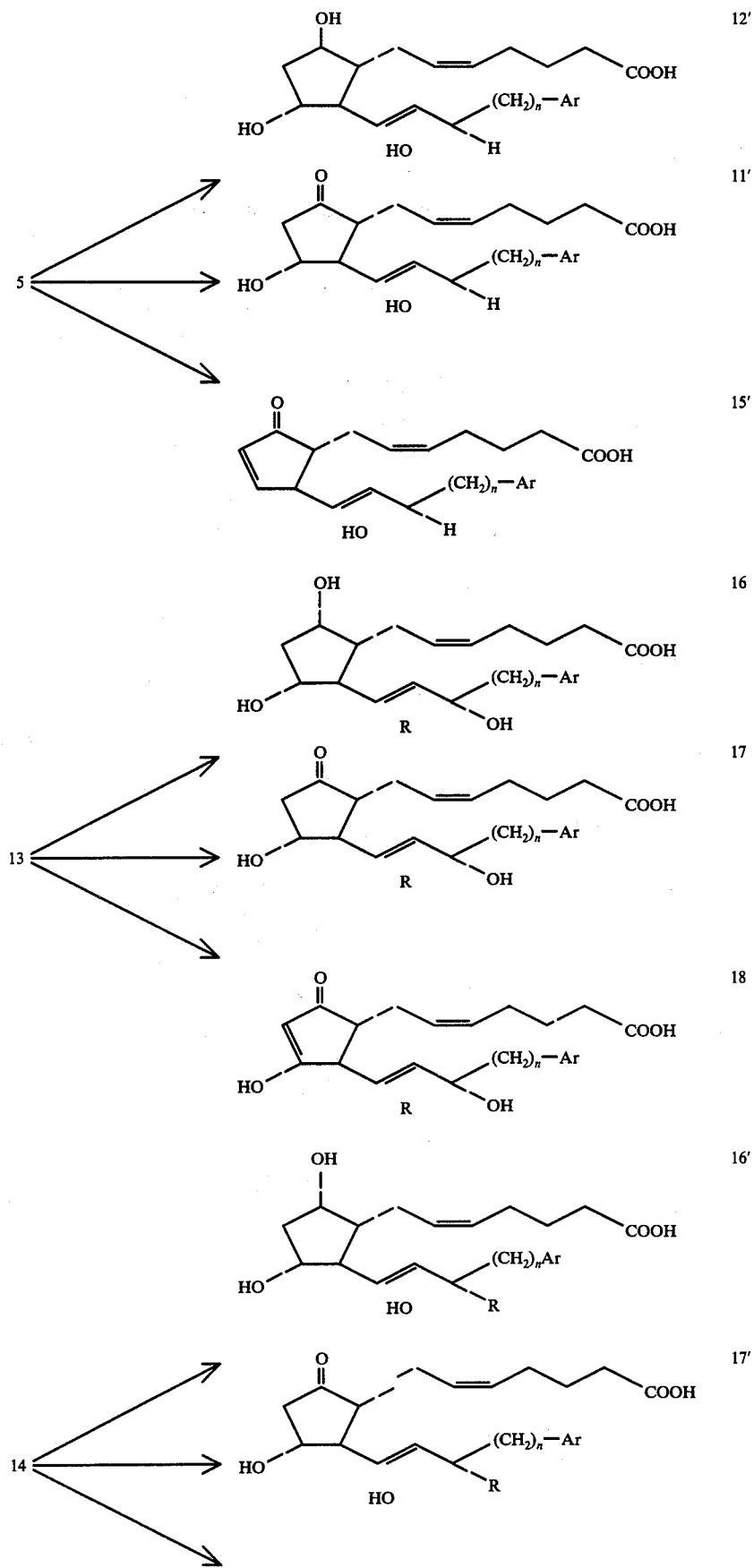

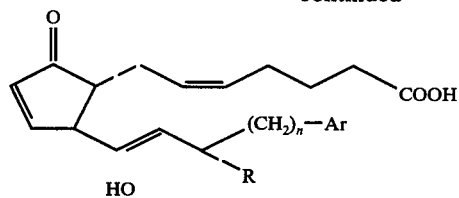

As is illustrated in scheme C, 5, 13 and 14 may be substituted for 4 in scheme B to provide prostaglandin derivatives 12′-18′.

Scheme D illustrates the synthesis of precursors to the 13,14-dihydro-15-substituted-ω-pentanorprostaglandins.

In 3→19 + 19′ the enone 3 is reduced to the tetrahydro compound through the use of any of the complex metal hydride reducing agents, LiAlH$_4$, NaBH$_4$, KBH$_4$, LiBH$_4$ and Zn(BH$_4$)$_2$. Especially preferred is NaBH$_4$. The products, 19 and 19′, are separated from each other by column or high pressure liquid chromatography.

Furthermore, the compounds 4 and 5 of Scheme A can be reduced catalytically with hydrogen to 19 and 19′ respectively. The stage at which the double bond is reduced is not critical, and hydrogenation of 6 or 7 of scheme B will also afford useful intermediates for the 13,14 dihydro prostaglandin analogs of the present invention. This reduction may be achieved with either a homogenous catalyst such as tristriphenylphosphinerhodiumchloride, or with a heterogeneous catalyst such as platinum, palladium or rhodium. In a similar way the precursors to the 15-lower alkyl-15-substituted-ω-pentanorprostaglandins are synthesized by substituting compounds 13 and 14 for 4 and 5 respectively, in the synthesis just described. The conversion of 19, 19′, 20′ and 20 to their respective prostaglandins follows the route shown in scheme B when 4 is replaced by 19, 19′, 20′ and 20 to yield the 13,14 -dihydro PGE$_2$, PGA$_2$ and PGF$_2$ series of prostaglandin derivatives containing hydrogen or lower alkyl group at carbon 15.

Scheme D

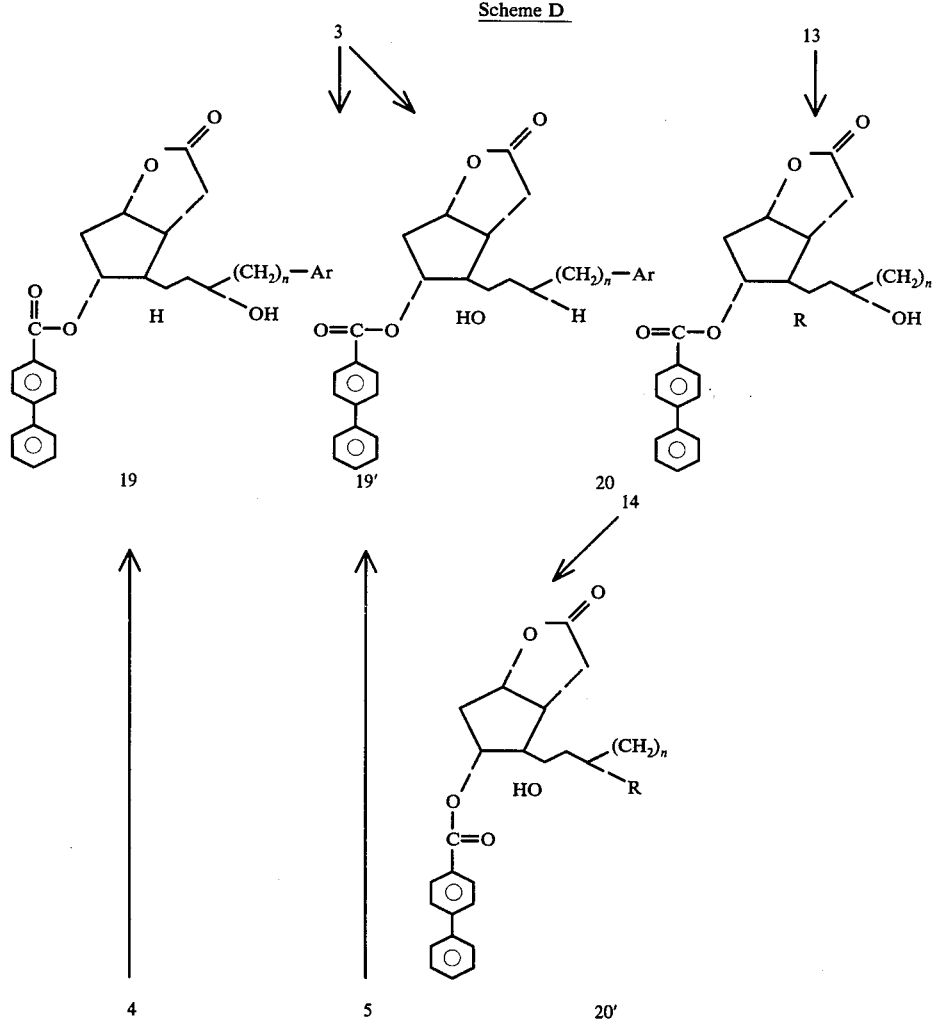

Scheme E illustrates the preparation of the various reduced 15-substituted-ω-pentanorprostaglandin precursors:

anti-fertility activity through a mechanism not affecting smooth muscle for example, luteolytic mechanisms.

The novel compounds of this invention possess highly selective activity profiles compared with the corresponding naturally occurring prostaglandins and, in many case, exhibit a longer duration of action. A prime example of the therapeutic importance of these prostaglandin analogs is the efficacy of 16-α-thienyl-ω-tetranorprostaglandin $E_2$ which exhibits hypotensive activity of enhanced potency and duration of action as compared with $PGE_2$ itself. At the same time, the smooth muscle stimulating activity is markedly depressed in comparison with $PGE_2$.

In a similar manner, the other 16-Ar-substituted $PGE_2$, $PGE_1$, $PGE_0$ (tetrahydro $PGE_2$) and 13,14 dihydro $PGE_2$ analogs, as well as the novel 15-substituted-ω-pentanorprostaglandins of the A series of the present invention exhibit desirable hypotensive activity. In addition, the 16-Ar-substituted prostaglandins of the E and A series are potent inhibitors of gastric acid secretion, useful for the treatment of peptic ulcers or gastric hyperacidity.

It should be noted that the 15-substituted 13,14-dihydro-ω-pentanorprostaglandins of this invention are especially useful owing to their increased selectivity. For example, the 16-Ar-substituted-ω-tetranor-13,14-dihydro $PGE_2$, have highly selective hypotensive activity whereas the 17-Ar-substituted-ω-trisnor 13,14 dihydro have highly selective smooth muscle activity. Furthermore, the 15-Ar-substituted-ω-pentanor 13,14-dihydro $E_2$ prostaglandins of the present invention are highly selective bronchodilator agents having no significant hypotensive activity.

17-α-furyl-ω-trisnorprostaglandin $F_{2α}$ and $E_2$ exhibits outstanding smooth muscle stimulating activity useful for fertility control, abortion and induction of labor, while at the same time having reduced blood pressure effects. Furthermore, the other novel 17-substituted-ω-trisnorprostaglandins of the E and F series, of this invention, i.e. the 17,18,19 and 20-Ar-substituted prostaglandins of the E and F series of this invention, exhibit desirable smooth muscle stimulating activity. The 16-Ar-substituted-ω-tetranorprostaglandins of the F series are useful for fertility control via mechanisms not affecting smooth muscle.

Furthermore, 16-β-thienyl-ω-tetranorprostaglandin $E_2$ exhibits high bronchodilator activity with reduced non-vascular smooth muscle activity. In a similar fashion, the other 16-Ar-substituted-ω-tetranorprostaglandin $E_1$ and $E_2$ analogs, for example, the 16-α-thienyl-ω-tetranorprostaglandin $E_1$ of the present invention also display desirable bronchodilator activity.

The novel 15 lower alkyl compounds of this invention have the same profile of activity as the prostaglandin analogs of this invention, where R is hydrogen, from which they are derived. Their special utility is concerned with the fact that their duration of action is much increased over the above said compounds, where R is hydrogen, and in such cases where this is essential the 15 lower alkyl compounds are usually preferred.

Especially useful by virtue of their selective action are the 13,14-dihydro 15-substituted-ω-pentanorprostaglandins. For example, the 15-Ar-substituted 13,14-dihydro prostaglandins of the E series are highly selective bronchodilators having no significant hypotensive activity. 16-Ar-substituted 13,14-dihydro tetranorprostaglandins of the E series are highly selective hypotensive agents with no significant bronchodilator activity.

The 17-substituted 13,14-dihydro prostaglandin of this invention have selective smooth muscle stimulating activity.

All of the prostaglandins of this invention are also useful in the forms of their salts with pharmaceutically acceptable cations. Furthermore, esters at $C_9$, $C_{11}$ and $C_{15}$ in which the acyl group is lower alkanoyl, formyl, or benzoyl, likewise share the utilities of the prostaglandin from which they are derived. In some cases a lower incidence of undesirable side effects accompanies the use of these esters as compared with the corresponding unesterified prostaglandins. It is obvious to one skilled in the art that these compounds include mono esters in the case of a prostaglandin of the A series, diesters in the case of prostaglandins of the E series and triesters in the case of the F series. Such esters are readily prepared by standard methods well known in the art. The prostaglandin analogs which have a beta hydroxyl at C15 and possess a C15 lower alkyl group have action which is similar to their epimers. In some cases, however, the selectivity that these compounds display exceeds that of the epimeric compounds.

The new compounds of this invention can be used in a variety of pharmaceutical preparations which contain the compound or a pharmaceutically acceptable salt thereof, and they may be administered in the same manner as natural prostaglandins by a variety of routes, such as intravenous, extra- and intra-amniotic, oral and topical, including aerosol, intravaginal, and intranasal, among others.

For induction of abortion an aqueous suspension of a 17-substituted-ω-trisnorprostaglandin of the E or F series or tablets would appropriately be administered at oral doses of about 1–20 mg., with 1–7 doses per day being employed. For intravaginal administration a suitable formulation would be lactose tablets or an impregnated tampon of the same agent. For such treatments suitable doses would be from about 1–20 mg./dose for the 17-α-furyl $PGE_2$ derivative or from about 10–200 mg/dose for the 17-α-furyl $PGF_{2α}$ derivative, with 1 to 7 doses being employed.

Alternatively, for abortion, the 17-substituted-ω-trisnorprostaglandins can be administered intra-amniotically at doses of 5–40 mg., 1–5 times per day, or infused intravenously at doses of 5–500 μg/minute for a period of from about 1–24 hours. Alternatively, for abortion, the 17-substituted-ω-trisnorprostaglandins can be administered by extra-amniotic infusion at doses of 0.5–50 μg/min. for a period of from 1–24 hours.

Another suitable use for the 17,18,19 and 20-Ar-substituted prostaglandin analogs of this invention is as inducers of labor. For this purpose an ethanol-saline solution of a 17-substituted-ω-trisnor $PGF_{2α}$ or $PGE_2$ derivative can be employed as an intravenous infusion in the amount of from about 0.05–50 μg/minute for from about 1–10 hours or orally in the form of capsules, tablets, solutions or suspensions at doses of 0.005–5 mg. with 1–7 doses being employed.

To produce bronchodilation, an appropriate dosage form would be an aqueous ethanolic solution of a 13,14-dihydro 15-Ar-substituted-ω-pentanorprostaglandin or 16-Ar-substituted-tetranor $PGE_1$ or $PGE_2$ employed as an aerosol using fluorinated hydrocarbons as propellant in the amount of from about 3–500 μg/dose with up to 16 doses per day. To increase nasal potency, an appropriate dosage form would be an aqueous solution of 16-Ar-substituted-tetranor $PGE_1$ or $PGE_2$, employed in 19→22 is carried out as illustrated on Scheme B for 4→9. 22 can be usd as both a precursor to a 13,14-dihydro 15-substituted-ω-pentanorprostaglandin of the "2-series" or as an intermediate to 23, a precursor to a 13,14-dihydro-15-substituted-ω-pentanorprostaglandin of the "1-series". 22→23 is carried out by catalytic hydrogenation using the catalyst described for the reduction of 4→19 of Scheme D. Intermediates of the type 21 are prepared by selective reduction of the 5-6 cis double bond at low temperature using catalysts such as those described for 4→19 and 17→23. Especially preferred for this reduction is the use of palladium on carbon as a catalyst and a reaction temperature of −20°. Intermediates of the type 21 are not only precursors to 15-substituted-ω-pentanorprostaglandins of the "1-series" through the route 9→15 of scheme B, but also as a precursor to compounds of the type 23 through the route already discussed for 22→23. Furthermore, the 15-substituted-ω-pentanorprostaglandins of the $E_1$ and $F_{1\alpha}$ series may be obtained directly from the corresponding prostaglandin analog of the "2-series" by first protecting the hydroxyl by introducing dimethyl isopropyl silyl groups, reducing selectively the cis double bond, and removing the protecting group.

from the appropriately substituted analogs of 9 and 19 whose syntheses follow those of Scheme A and B.

13,14-dihydro-15-lower alkyl-15-substituted-ω-pentanorprostaglandins are available from the appropriately substituted precursors via Scheme E.

In the foregoing procedures, where purification by chromatography is desired, appropriate chromatographic supports include neutral alumina and silica gel and 60-200 mesh silica gel is generally preferred. The chromatography is suitably conducted in reaction-inert solvents such as ether, ethyl acetate, benzene, chloroform, methylene chloride, cyclohexane and n-hexane, as further illustrated in the appended examples.

In numerous in vivo and in vitro tests we have demonstrated that the new prostaglandin analogs possess physiological activities comparable to those exhibited by the natural prostaglandins (see above). These tests include, among others, a test for effect on isolated smooth muscle from guinea pig uterus, ginea pig ileum and rat uterus, inhibition of norepinephrine-induced lipolysis in isolated rat fat cells, inhibition of histamine-induced bronchospasm in the guinea pig effect, on dog blood pressure, inhibition of stress-induced ulceration in the rat, inhibition of pentagastrine-induced hydrochlo-

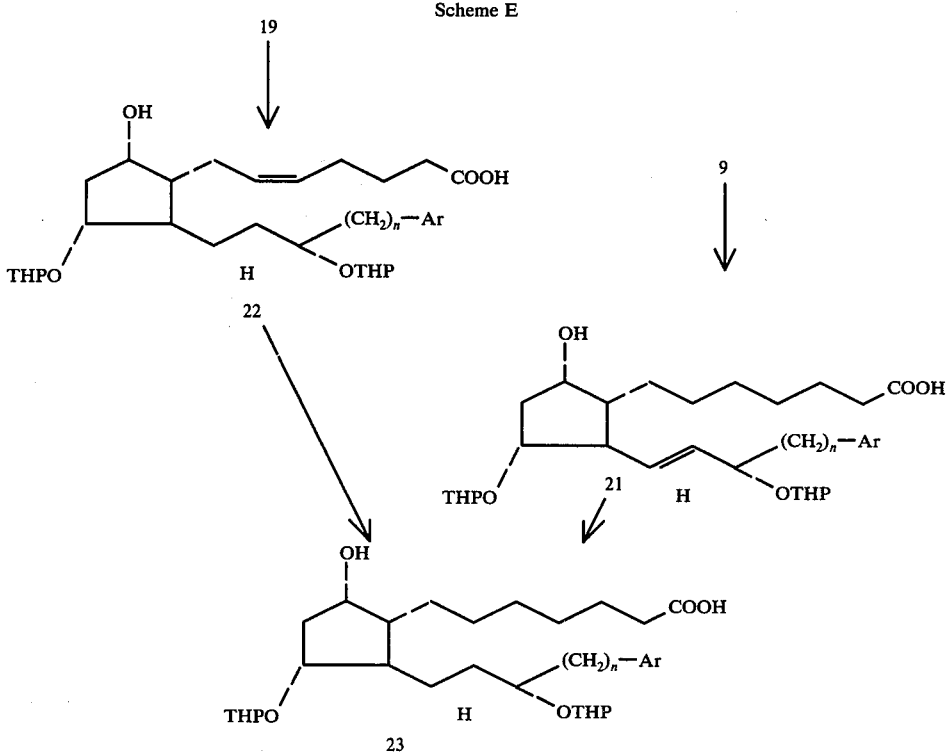

Scheme E

The introduction of the protecting group is usually accomplished by treatment of the prostaglandin analog with dimethyl isopropyl chlorosilane and 1,1,3,3-tetramethyl-1,3-diisopropyl disilazane, the reduction is accomplished as discussed above for 9→21 and removal of the protecting group is accomplished by contacting the reduced protected compound with 3:1 acetic acid:-water for 10 minutes or until reaction is substantially complete.

The $C_{15}$ epimers of 21, 22 and 23 can be used as precursors to the 15-epi series of prostaglandin derivatives described above, and 15-lower-alkyl-15-substituted-ω-pentanorprostaglandins reduced at the 5,6 and/or the 3,114 position and their $C_{15}$ epimers can be prepared ric acid reaction in rat and dog, inhibition of ADP- or collagen-induced aggreation of blood platelets, and on diarrhea in mice.

The physiological responses observed in these tests are useful in determining the utility of the test substance for the treatment of various natural and pathological conditions. Such determined utilities include: antihypertensive activity, bronchodilator activity, vasodilator activity, antithrombogenic activity, antiarrhythmic activity, cardiac stimulant activity, antiulcer activity, smooth muscle activity [useful as an antifertility agent, for the induction of labor, and as an abortifacient], and the form of nose drops in the amount of 1-100 μg/dose as needed.

The 16-Ar-substituted-ω-tetranorprostaglandins of the E,A, and 13,14-dihydro E and A series are useful antiulcer agents. For the treatment of peptic ulcers, these drugs are appropriately administered orally in the form of aqueous suspensions, ethanolic solutions or preferably in the form of capsules or tablets at doses of 0.001 to 0.10 mg/kg per dose with up to 12 doses per day.

The 16-Ar-substituted-ω-tetranorprostaglandins of the $E_1$, $E_2$, $E_0$ and 13,14-dihydro E and A series, are useful hypotensive agents. For treatment of hypertension these drugs could appropriately be administered as an intravenous injection at doses of about 0.5–10 μg/kg or preferably in the form of capsules or tablets at doses of 0.005 to 0.5 mg/kg/day.

The above named 15-substituted-ω-pentanorprostaglandin of the "one" series with the proviso that $n = 1$ to 5 may be prepared by the synthetic route outlined in Scheme F. In the first step the hemiacetal U is caused to react with the 4-carbohydroxy-n-butyl triphenylphosphonium bromide to produce intermediate W.

W→X involves treatment with diazomethane; followed by acetic anhydride and pyridine; followed by reduction with palladium in carbon in ethanol:acetic acid; followed by oxidation with dimethyl sulfoxide, dicyclohexylcarbodiimide, and pyridinium trifluoroacetate.

X→Y involves treatment with the sodium or lithium salt of the appropriate phosphonate (2) and purification by column chromatography.

Y→Z involves reduction with zinc borohydride or lithium triethylborohydride, hydrolysis, and separation of the C15 epimers by column chromatography.

Z→Z1 involves treatment with dihydropyran with an acid catalyst followed by mild aqueous base hydrolysis.

Z1 $PGF_{1\alpha}$, $PGE_1$, and $PGA_1$ 15-substituted-ω-pentanorprostaglandins follows exactly the same method as outlined for the $PGF_{2\alpha}$, $PGE_2$, $PGA_2$ series above.

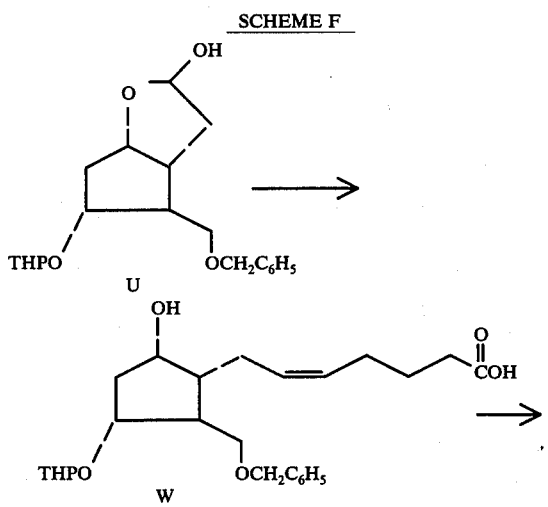

SCHEME F

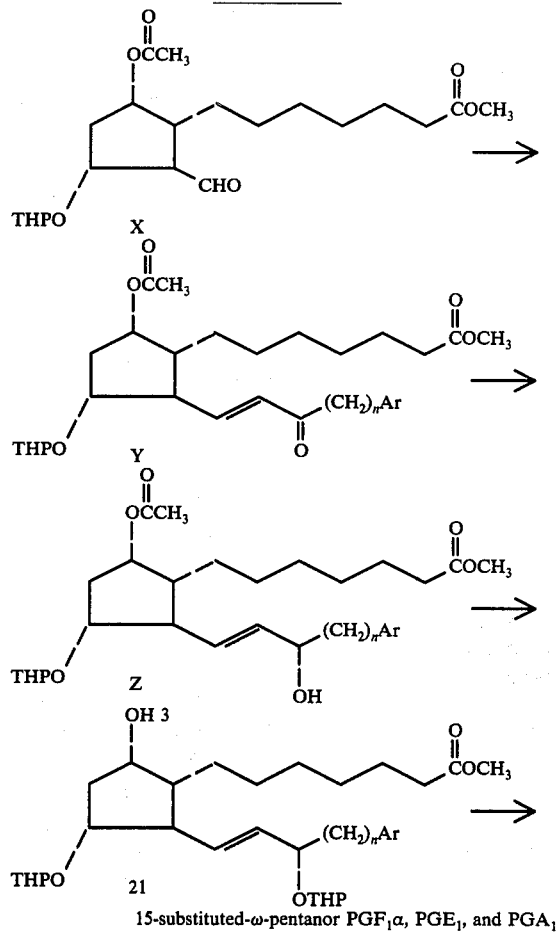

15-substituted-ω-pentanor $PGF_1\alpha$, $PGE_1$, and $PGA_1$

Each of the novel compounds of the present invention are also useful in the form of their $C_1$ esters. Examples of preferred esters are those wherein the esterifying group is alkyl of from one to twelve carbon atoms; cycloalkyl of from three to eight carbon atoms; aralkyl of from seven to nine carbon atoms; phenyl or β-naphthyl or mono substituted phenyl or β-naphthyl wherein said substituent is:

halo, lower alkyl, lower alkoxyl or phenyl. Especially preferred are the p-biphenyl esters. These specific esters are valuable because they are very easily crystallized, thereby affording the opportunity to recover them in highly pure form and outstanding yield whereas prostaglandins in general ordinarily present severe crystallization problems. The newpara-biphenyl esters exhibit the activities of the corresponding parent novel compounds and in addition possess the advantage of a flattened activity versus time curve which is often advantageous. They furthermore have reduced effects on gastrointestinal smooth muscle as evidenced by the reduction of side effects such as diarrhea. The new compounds in the form of the para-phenylphenol esters are prepared by procedures already described with appropriate substitution of corresponding intermediates in para-phenylphenol ester from for the intermediates employed in the foregoing reaction schemes. Thus, for example, compounds 9 and 10 may be esterified with para-phenylphenol in the presence of dicyclohexylcarbodiimide to provide para-phenylphenol esters of precursors to 15-substituted-ω-pentanorprostaglandin para-phenylphenol esters. These can, through steps 9–12, 10–11 and 11–12, be converted to the novel para-phenylphenol esters mentioned above. Further, compounds 11, 12 and 15 can likewise be esterified with para-phenylphenol and dicyclohexylcarbodiimide to provide the desired esters. In addition, the para-biphenyl ester moiety can be introduced at an earlier stage by using in step 8–9 a tri-para-phenylphenol ortho ester phosphonium bromide of the structure $[(C_6H_5)_3P \oplus CH_2CH_2CH_2CH_2C(OR)_3]Br \ominus$, wherein R equals para-phenylphenyl to provide the corresponding ortho ester of 9 which can be carried through steps 9–15 to yield the desired para-phenylphenol esters.

To prepare any of the above dosage forms or any of the numerous other forms possible, various reaction-inert diluents, excipients or carriers may be employed. Such substances include, for example, water, ethanol, gelatins, lactose, starches, magnesium stearate, talc, vegetable oils, benzyl alcohols, gums, polyalkylene glycols, petroleum jelly, cholesterol, and other known carriers for medicaments. If desired, these pharmaceutical compositions may contain auxiliary substances such as preserving agents, wetting agents, stabilizing agents, or other therapeutic agents such as antibiotics.

The following examples are merely illustrative, and in no way limit the scope of the appended claims. In these examples it will be appreciated that all temperatures are expressed in Centigrade, all melting and boiling points are uncorrected and all biological test data is expressed in terms of % activity of $PGE_2$ or administered at the same level (i.e., $PGE_2 = 100$) unless otherwise noted.

The biological data given below was obtained using the following test procedures:

Histamine-Induced Bronchoconstriction—Guinea Pigs

Bronchodilator activities were evaluated in conscious female Reed-Willet guinea pigs (200 to 250 g) fasted overnight according to the method of Van Arman, Miller and O'Malley (1). At a pre-selected interval (pre-challenge interval) following oral or aerosol administration of water or the test drug in water, each animal was challenged with histamine aerosol as follows: a 0.4% aqueous solution of histamine was placed in a Vaponephrine Standard Nebulizer (Vaponephrine Company, Edison, New Jersey) and sprayed under an air pressure of 6 lb/in$^2$ into a closed 8 × 8 × 12 inch transparent plastic container for one min. Immediately thereafter, the guinea pig was placed in the container. The respiratory status (a reflection of bronchoconstriction) of the guinea pig after one min in the container was scored as follows: 0, normal breathing; 1, slightly deepened breathing; 2, labored breathing; 3, severely labored breathing and ataxia; 4, unconsciousness. The scores for a control group and a test group (8 animals/group) were summed and compared and the difference expressed as percent protection. (1)

1. VAN ARMAN, C. G., Miller, L. M. and O'Malley, M. P.: SC-10,049: a catacholamine bronchodilator and hyperglycemic agent. J. Pharmacol. Exp. Ther. 133 90–97, 1961.

Dog Blood Pressure

Mongrel dogs were anesthetized with sodium pentobarbitol, 30 mg/kg/i.v. Femoral artery blood pressure was measured with a mercury manometer and recorded on smoked paper and heart rate was determined from electrocardiograms recorded from subcutaneous electrodes. Drugs were given through a cannula in a femoral vein.

Isolated Gastrointestinal and Reproductive Tissue

All measurements were made in a 2 ml tissue bath using a Phipps-Bird Linear Motion Transducer model ST-2. Tissues were allowed to respond to a stable maximum, at which point they were washed and allowed to return to baseline condition. All determinations, are an average of at least three individual tissues at each reported dose. Data for analogs were compared to the dose response obtained for a natural PG in a given tissue. For purposes of potency comparisons, a standard dose of natural PG was selected; and all responses were calculated as a percentage of its response. Additional data were recorded as minimum effective dose (MED) and a consistently effective dose (CED) to establish compound detection levels for each tissue. A standard equivalent dose (SED) was determined. This value was defined as the amount of compound (ng/ml) which yielded a response that was equivalent to the tissue's response to a given dose of standard PG.

Guinea Pig Ileum

The ileum was dissected from 200–300 g male guinea pigs sacrificed by cervical dislocation. The tissue was suspended in 2 ml Tyrode solution (2) at 37° C. $PGE_2$ (30 ng/ml and/or $PGF_{2\alpha}$ (30 ng/ml) were used to establish tissue activity.

2. Hale, L. J. ed. *Biol. Lab Data.* p. 92, 1958.

Guinea Pig Uterus (3)

Nulliparous females (300–400 g) which were not in estrus were sacrificed by cervical dislocation. The dissected uteri were incubated in 2 ml of a modified Krebs solution (12) at 37° C. Uterine activity was established using $PGE_2$ (1.0 ng/ml) and/or $PGF_{2\alpha}$ (10 ng/ml).

3. Clegg, P. C., P. Hopkinson and V. R. Pickles. H. Physiol. 167:1, 1963.
4. W. S. Umbreit, R. H. Burris and J. F. Stauffer. Monometric Techniques 148, 1957.

EXAMPLE 1

Dimethyl 2-Oxo-3-(2-thienyl)propylphosphonate (2a)

A solution of 37.2 g (0.3 mole) dimethyl methylphosphonate (Aldrich) in 400 ml dry tetrahydrofuran was cooled to $-78°$ in a dry nitrogen atmosphere. To the stirred phosphonate solution was added 194 ml of 1.6 M n-butyllithium in hexane solution (Alfa Inorganics, Inc.) dropwise over a period of 18 minutes at such a rate that the reaction temperature never rose above $-65°$. After an additional 5 minutes stirring at $-78°$, 23.4 g (0.15 mole) methyl 2-(2-thienyl)acetate was added dropwise at a rate that kept the reaction temperature less than $-70°$ (20 minutes). After 3.5 hours at $-78°$ the reaction mixture was allowed to warm to ambient temperature, neutralized with 6 ml acetic acid and rotary evaporated to a white gel. The gelatinous material was taken up in 75 ml water the aqueous phase extracted with 100 ml portions of chloroform (3x) the combined organic extracts were backwashed (50 ml $H_2O$), dried ($MgSO_4$), and concentrated (water aspirator) to a crude residue and distilled, b.p. 150°–152° (<0.5 mm) to give 4.8 g dimethyl 2-oxo-3-(2-thienyl)propylphosphonate (2a).

The nmr spectrum ($CDCl_3$) showed a doublet centered at 3.7δ (J = 11.0 cps, 6H) for

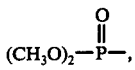

a singlet at 4.12δ (2H) for Ar-CH₂-CO-,
a doublet centered at 3.16δ (J = 22 cps, 2H)

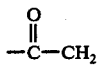

and a multiplet at 6.8–7.3δ (3H) for the thienyl protons. In the same manner the corresponding 3-thienyl compound was prepared NMR data 3.65δ (J = 11 cps), 3.1δ (J = 24 cps).

EXAMPLE 2

2-[3α-p-phenylbenzoyloxy-5α-hydroxy-2β(3-oxo-4-(2-thienyl)-trans-1-buten-1-yl)-cyclopent-1α-yl]acetic acid, γ-lactone (3a)

Dimethyl 2-oxo-3-(2-thienyl)propylphosphonate (2a) (6.4 g, 25.7 mmole) in 300 ml. anhydrous ether was treated with 7.7 ml. (18 mmole) 2.34 M n-butyllithium in n-hexane (Alfa Inorganics, Inc. in a dry nitrogen atmosphere at room temperature. After 5 min. of stirring, an additional 300 ml. of anhydrous ether was added, followed by 6.0 g. (17 mmole) 2-[3α-p-phenylbenzoyloxy-5α-hydroxy-2β-formylcyclopent-1α-yl]acetic acid, γ-lactone in one portion and 50 ml. anhydrous ether. After 35 minutes, the reaction mixture was quenched with 5 ml. glacial acetic acid and washed with 100 ml. saturated brine (1x), dried (MgSO₄) and evaporated to yield 3.28 g. 2-[3α-p-phenylbenzoyloxy-5α-hydroxy-2β-(3-oxo-4-(2-thienyl)-trans-1-buten-1-yl)cyclopent-1α-yl]acetic acid, γ-lactone (3a) as an oil after column chromatography (silica gel, Baker, 60–200 mesh).

The ir spectrum (CHCl₃) of the product exhibited adsorbtion bands at 1770 cm⁻¹ (strong), 1705 cm⁻¹ (strong), 1675 cm⁻¹ (medium) and 1625 cm⁻¹ (medium) attributable to the carbonyl groups and at 970 cm⁻¹ for the trans double bond. The nmr spectrum (CDCl₃) exhibited a doublet centered at 6.27 (1H, J-16 cps) for the olefinic proton, a singlet at 4.01 (2H) for Ar-CH₂-C, and multiplets at 4.90–5.50 (2H) and 2.05–3.20 (6H) for the remainder of the protons. In the same manner the corresponding 3-thienyl compound was prepared having IR bands at 1715, 1775, 1630, 1670 and 970 cm⁻¹.

The product (3a) may also be converted to 15-lower alkyl-16-(2-thienyl)-ω-tetranorprostaglandins of the A, E or F series by the procedures of examples 4–12 and 14–20.

13,14 Dihydro-15-lower alkyl-16(2-thienyl)-ω-tetranorprostaglandins of the A, E or F series may be obtained from (3a) via the procedures of examples 4–12, 14, and 19–20.

EXAMPLE 3

2-[3α-Phenylbenzoyloxy-5α-hydroxy-2β-(3α-hydroxy-4-(2-thienyl)-trans-1-buten-1yl]acetic acid, γ-lactone (4a) and
2-[3α-p-Phenylbenzoyloxy-5α-hydroxy-2β-(3β-hydroxy-4-(2-thienyl)-trans-1-buten-1-yl)cyclopent-1α-yl]acetic acid, γ-lactone (5a)

To a solution of 4.7 g. (10 mmole) 2-[3α-p-phenylbenzoyloxy-5α-hydroxy-2β-(3-oxo-4-(2-thienyl)-trans-1-buten-1-yl) cyclopent-1α-yl]acetic acid, γ-lactone (3a) in 30 ml. dry 1,2-dimethoxyethane in a dry nitrogen atmosphere at ambient temperature was added dropwise 10 ml. of a 0.5 M zinc borohydride solution. After stirring at room temperature for 1 hour, a saturated sodium bitartrate solution was added dropwise until hydrogen evolution ceased. The reaction mixture was allowed to stir for 5 minutes at which time 200 ml. dry methylene chloride was added. After drying (MgSO₄) and concentrating (water aspirator), the resultant semisolid was purified by column chromatography on silica gel (Baker "Analyzed" Reagent 60–200 mesh) using ether as eluent. After elution of less polar impurities, a fraction containing 710 mg. 2-[3α-p-Phenylbenzoyloxy-5α-hydroxy-2β-(3α-hydroxy-4-(2-thienyl)-trans-1-buten-1-yl)cyclopent-1α-yl]acetic acid, γ-lactone (4a), a 50 mg. fraction of mixed 4 and 5 and finally a fraction (862 mg.) of 2-[3α-p-phenylbenzoyloxy-5α-hydroxy-2β-(3β-hydroxy-4-(2-thienyl)-trans-1-buten-yl)cyclopent-1α-yl]acetic acid, γ-lactone (5a).

The ir spectrum (CHCl₃) of 4 had strong carbonyl adsorbtions at 1770 and 1710 cm⁻¹ and an adsorbtion at 965 cm⁻¹ for the trans double bond. In the same manner the corresponding 3-thienyl compound was prepared from the appropriate starting material. α-Hydroxyl epimer (less polar on TLC) m.p. 101.5°–102.5 ° C. β-Hydroxyl epimer (more polar on TLC) m.p. 109°–111° C. The compounds were crystallized from EtAc-pentane.

EXAMPLE 4

2-[3α,5α-Dihydroxy-2β-(3α-hydroxy-4-(2-thienyl)-trans-1-buten-1-yl)cyclopent-1α-yl]acetic acid, γ-lactone (6a)

A heterogeneous mixture of 1.35 g (2.85 mmole) of 2-[3α-p-phenylbenzoyloxy-5α-hydroxy-2β-(3α-hydroxy-4-(2-thienyl)-trans-1-buten-1-yl)cyclopent-1α-yl]acetic acid, γ-lactone (4a), 13 ml. of absolute methanol and 394 mg of finely powered, anhydrous potass carbonate was stirred at room temperature for 1 hour, then cool to 0°. To the cooled solution was added 5.6 ml of 1.0N aqueous hydrochloric acid. After stirring at 0° for an additional 10 minutes, 15 ml. of water was added with concomitant formation of methyl p-phenylbenzoate which was collected by filtration. The filtrate was saturated with solid sodium chloride, extracted with ethyl acetate (4 × 20 ml.), the combined organic extracts were washed with saturated sodium bicarbonate (10 ml.), dried (MgSO₄) and concentrated to give 738 mg of viscous, oily 2-[3α,5α-dihydro-2β-(3α-hydroxy-4-(2-thienyl)-trans-1-buten-1-yl)cyclopent-1α-yl]acetic acid, γ-lactone (6a).

The ir spectrum (CHCl₃) exhibited a strong adsorption at 175 cm⁻¹ for the lactone carbonyl and medium adsorption at 965 cm⁻¹ for the trans-double bond. In the same manner the corresponding 3-thienyl compounds were prepared. 15-αOH IR 1774, 970 cm⁻¹. 15-βOH I 1775, 970 cm⁻¹.

EXAMPLE 5

2-[5α-Hydroxy-3α-(tetrahydropyran-2-yloxy)-2β-(3α-(tetrahydropyran-2-yloxy)-4-(2-thienyl)-trans-1-buten-1-yl)cyclopent-1α-yl]acetic acid, γ-lactone (7a)

To a solution of 738 mg (2.5 mmole) 2-[3α,5α-dihydroxy-2β-(3α-hydroxy-4-(2-thienyl)-trans-1-buten-yl)cyclopent-1α-yl]acetic acid, γ-lactone (6a) in 5 ml. anhydrous methylene chloride and 0.5 ml. of 2,3-dihydropyran at 0° in a dry nitrogen atmosphere was added 7 mg p-toluenesulfonic acid, monohydrate. After stirring for 15 minutes, the reaction mixture was combined with 100 ml. ether, the ether solution washed with saturated sodium bicarbonate (1 × 15 ml) then saturated brine (1 × 25 ml.), dried (MgSO$_4$) and concentrated to yield 1.2 g (>100%) crude 2-[5α-hydroxy-3α-(tetrahydropyran-2-yloxy)-2β-(3α-(tetrahydropyran-2-yloxy)-4-(2-thienyl)-trans-1-buten-1-yl)cyclopent-1α-yl]acetic acid, γ-lactone (7a).

The ir (CHCl$_3$) spectrum displayed a medium absorbtion at 970 cm$^{-1}$ for the trans-double bond and at 1772 cm$^{-1}$ for the lactone carbonyl.

In the same manner the corresponding 3-thienyl compounds were prepared.
    15α-OTHP, IR 1770, 970 cm$^{-1}$.
    15β-OTHP, IR 1770, 970 cm$^{-1}$.

EXAMPLE 6

2-[5α-Hydroxy-3α-(tetrahydropyran-2-yloxy)-2β-(3α-{tetrahydropyran-2-yloxy}-4-phenyl-trans-1-buten-1yl)cyclopent-1α-yl]acetaldehyde, γ-hemiacetal (8a)

A soluton of 1.2 g (2.5 mmole) 2-[5α-hydroxy-3α-(tetrahydropyran-2-yloxy)-2β-(3α-{tetrahydropyran-2-yloxy}-4-(2-thienyl)-trans-1-buten-1-yl)cyclopent-1α-yl] acetic acid, γ-lactone (7a) in 25 ml dry toluene was cooled to −78° in a dry nitrogen atmosphere. To this cooled solution was added 3.4 ml of 0.8 M diisobutylaluminum hydride in n-hexane (Alfa Inorganics) dropwise at such a rate so that the internal temperature never rose above −65° L (15 minutes). After an additional 45 minutes of stirring at −78°, anhydrous methanol was added until gas evolution ceased and the reaction mixture was allowed to warm to room temperature. The reaction mixture was combined with 150 ml ether, washed with 50% sodium potassium tartrate solution (4 × 20 ml), dried (Na$_2$SO$_4$) and concentrated to a quantitative yield of oily 2-[5α-hydroxy-3α-(tetrahydropyran-2-yloxy)-2β-(3α-{tetrahydropyran-2-yloxy}-4-(2-thienyl)-trans-1-buten-1-yl)cyclopent-1-yl]acetaldehyde, γ-hemiacetal (8a). The ir spectrum displayed a broad absorption at 3400 cm$^{-1}$ for the hydroxyl group. In the same manner the corresponding 3-thienyl compounds were prepared.
    15α-OTHP, IR: 970 cm$^{-1}$.
    15β-OTHP, IR: 970 cm$^{-1}$.

EXAMPLE 7

9α-Hydroxy-IIα,15α-bis-(tetrahydropyran-2-yloxy)-16-(2-thienyl)-cis-5-trans-13-ω-tetranor-prostadienoic Acid (9a)

To a solution of 2.6 g (6 mmole) (4-carbohydroxy-n-butyl) triphenylphosphonium bromide in a dry nitrogen atmosphere in 5.0 ml. dry dimethyl sulfoxide was added 5.7 ml. (11.4 mmole) of a 2.2M solution of sodium methylsulfinylmethide in dimethyl sulfoxide. To this red ylide solution was added dropwise a solution of 1.03 g. (2.2 mmole) 2-[5α-hydroxy-3α-(tetrahydropyran-2-yloxy)-2β-(3α-[tetrahydropyran-2-yloxy]-4-(2-thienyl)-trans-1-buten-1-yl cyclopent-1α-yl]acetaldehyde, γ-hemiacetal (8a) in 5.0 ml. dry dimethyl sulfoxide over a period of 20 minutes. After an additional 2 hours stirring at room temperature, the reaction mixture was poured into ice water. The basic aqueous solution was washed twice with ethyl acetate (20 ml.) and acidified to pH∼3 with 10% aqueous hydrochloric acid. The acidic solution was extracted with ethyl acetate (3 × 20 ml.) and the combined organic extracts washed once with water (10 ml.), dried (MgSO$_4$) and evaporated to a solid residue. This solid residue was triturated with ethyl acetate and the filtrate concentrated to yield 1.02 g. of 9α-hydroxy-11α,15α-bis-(tetrahydropyran-2-yloxy)-16-(2-thienyl)-cis-5-trans-13-ω-tetranorprostadienoic acid 9a. The ir spectrum displayed a strong band at 1700 cm$^{-1}$ along with absorptions between 2800 to 2600 cm$^{-1}$ for the carboxyl group.

In the same manner the corresponding 3-thienyl compounds were prepared.
    15α-OTHP, IR: 1710, 970 cm$^{-1}$.
    15β-OTHP, IR: 1710, 970 cm$^{-1}$.

EXAMPLE 8

9-Oxo-11α,15α-bis-(tetrahydropyran-2-yloxy)-16-(2-thienyl)-cis-5-trans-13-ω-tetranor-prostadienoic Acid (10a)

To a solution cooled to −10° under nitrogen of 1.02 g (1.86 mmole) 9α-hydroxy-11α,15α-bis-(tetrahydropyran-2-yloxy)-16-(2-thienyl)-cis-5-trans-13-ω-tetranor-prostadienoic acid (9a) in 18 ml. reagent grade acetone was added dropwise to 0.82 ml. (2.04 mmole) of Jones' reagent. After 20 minutes at −10°, 0.260 m 2-propanol was added and the reaction mixture was allowed to stir an additional 5 minutes at which time it was combined with 75 ml. ethyl acetate, washed with water (3 × 10 ml.), dried (MgSO$_4$) and concentrated to give 952 mg. of 9-oxo-11α,15α-bis-(tetrahydropyran-2-yloxy)-16-(2-thienyl)-cis-5-trans-13-ω-tetranor-prostadienoic acid (10a), which was chromatographed on silica gel using ethyl acetate as eluent to afford 760 mg of pure 10a. In the same manner both the corresponding 3-thienyl compounds epimeric at C$_{15}$ were prepared.

EXAMPLE 9

9-Oxo-11α,15α-dihydroxy-16-(2-thienyl)-cis-5-trans-13-ω-tetranorprostadienoic Acid (11a)

A solution of 760 mg. (1.39 mmole) 9-oxo-11α,15α-bis-tetrahydropyran-2-yloxy)-16-(2-thienyl)-cis-5-trans-13-ω-tetranorprostadienoic acid (10a) in 3.0 ml. of a 65:35 mixture of glacial acetic acid:water was stirred under nitrogen at 25° for 18 hour then was concentrated by rotary evaporation. The resultant crude oil was purified by column chromatography on silica gel (Mallinckrodt CC-4 100-200 mesh) using ethyl acetate as eluent. After elution of less polar impurities the oily 9-oxo-11α,15α-dihydroxy-16-phenyl-cis-5-trans-13-ω-tetranor-prostadienoic acid (11a) weighing 369 mg. was collected.

IR displayed carbonyl absorbtions at 1730 and 1705 cm$^{-1}$, and a weak band at 972 cm$^{-1}$ for the 13,14-trans double bond.

The product of this example (11a) can be converted to 16-(2-thienyl)-ω-tetranorprostaglandins E$_1$, E$_0$, A$_2$, A$_1$ and A$_0$ via the procedures of examples 12, 19 and 20. In the same manner the corresponding 3-thienyl compounds were prepared.
    15α-OH, IR: 1715, 1740, 970 cm$^{-1}$.
    15β-OH, IR: 1715, 1740, 970 cm$^{-1}$.

Biological Activity: Guinea pig uterus 2-4; bronchodilator test 63; dog blood pressure 200.

EXAMPLE 10

9α,11α,15α-Trihydroxy-16-(2-thienyl)-cis-5-trans-13-ω-tetranorprostadienoic Acid (12a)

A mixture of 0.76 g. of 9α-hydroxy-11α,15α-bis-(tetrahydropyran-2-yloxy)-16-(2-thienyl)-cis-5-trans-13-ω-tetranorprostadienoic acid (9a) in 5 ml. of a 65:35 mixture of acetic acid: water is stirred under nitrogen at room temperature overnight, then is concentrated under reduced pressure to a viscous oil. The crude product is purified by column chromatography on Mallinckrodt CC-4 silica gel using ethyl acetate as eluent. After elution of less polar impurities, the desired 9α,-11α,15α-trihydroxy-16-(2-thienyl)-cis-5-trans-13-ω-tetranorprostadienoic acid (12a) is obtained as a viscous, colorless oil weighing 51 mg.

The product obtained above (12a) may be converted to 16-(2-thienyl)-ω-tetranorprostaglandin $F_{1\alpha}$ via the process of Example 20. 12a may also be converted to 16-(2-thienyl)-ω-tetranorprostaglandin $F_{0\alpha}$, via the process of Example 19.

EXAMPLE 11

2-[3α-p-Phenylbenzoyloxy-5α-hydroxy-2β-(3α-hydroxy-3β-methyl-4-(2-thienyl)-trans-1-buten-1-yl)cyclopent-1α-yl]acetic acid, γ-lactone (13a) and 2-[3α-p-Phenylbenzoyloxy-5α-hydroxy-2β-(3β-hydroxy-3α-methyl-4-(2-thienyl)-trans-1-buten-1-yl)cyclopent-1α-yl]acetic Acid γ-lactone (14a)

To a solution of 3190 mg. (6.2 mmole) 2-[3α-p-phenylbenzoyloxy-5α-hydroxy-2β-(3-oxo-4-(2-thienyl)-trans-1-buten-1-yl) cyclopent-1α-yl]acetic acid, γ-lactone (3a) in 26 ml. anhydrous ether and 20 ml. of tetrahydrofuran (distilled from LAH) in a dry nitrogen atmosphere at −78° is added dropwise 6.8 ml. of (0.92M) methyllithium in ether (Alfa). After stirring at −78° for 15 minutes the reaction is quenched by the dropwise addition of glacial acetic acid until the pH of the reaction is approximately 7. The mixture is then diluted with methylene chloride and the diluted organic solution is washed with water (1x) and with saturated brine (1x), is dried (anhydrous magnesium sulfate), and is concentrated to afford the epimeric alcohols.

The crude product is purified by column chromatography on silica gel to provide the 2-[3α-p-phenylbenzoyloxy-5α-hydroxy-2β-(3α-hydroxy-3β-methyl-4-(2-thienyl)-trans-1-buten-1-yl) cyclopent-1α-yl]acetic acid, γ-lactone (13a), and 2-[3α-p-phenylbenzoyloxy-5α-hydroxy-2β-(3β-hydroxy-3α-methyl-4-(2-thienyl)-trans-1-buten-yl)cyclopent-1α-yl]acetic acid, γ-lactone (14a).

This material (14a) may be converted to the 15β methyl-16-2-(thienyl)-ω-tetranorprostaglandins of the A, E, and F series by the procedures outlined in Examples 4–10 and 12–20.

Other lower alkyl derivatives of the type (14a) may be prepared by substituting the appropriate alkyl lithium derivative for methyl lithium in the above procedure. These derivatives are suitable for conversion to 15 lower-alkyl 16-2(thienyl-ω-tetranorprostaglandins of the A, E, and F series through the sequences of Example 3–10 and 12–20.

EXAMPLE 12

9-oxo-15α-hydroxy-16-2(thienyl)-cis-5-$\Delta^{10,11}$-trans-13-ω-tetranorprostatrienoic Acid (15a)

A solution of 55 mg. of 9-oxo-11α,15α-dihydroxy-16-2(thienyl)-cis-5-trans-13-ω-tetranorprostadienoic acid (11a) in 10 ml. dry methylene chloride and 10 ml. formic acid is stirred at room temperature for 5 hours. The reaction mixture is diluted with 50 ml. toluene and evaporated to yield (after chromatography) 9-oxo-11α-hydroxy-16-2(thienyl)-cis-5-$\Delta^{10,11}$-trans-13-ω-tetranorprostarienoic acid (15a).

In the same way 16-substituted-ω-pentanorprostaglandins of the $A_1$, $A_0$ and 13,14 dihydro $A_2$ series may be prepared from 16-substituted-ω-pentanorprostaglandins of the $E_1$, $E_0$ and 13,14-dihydro series respectively.

EXAMPLE 13

The procedure of example 3 in which sodium borohydride is substituted for zinc borohydride may be used to produce 19a. 19a may then be converted to 24a via the procedure of example 4, which is further converted to 13,14 dihydro-16-2(thienyl)-ω-tetranorprostaglandins of the A, E or F series by the procedures of examples 15–18, 10, and 12.

EXAMPLE 14

2-[5α-Hydroxy-3α-(tetrahydropyran-2-yloxy)-2β-(3α-[tetrahydropyran-2-yloxy]-4-(2-thienyl)but-1-yl)cyclopent-1α-yl]acetic Acid, γ-lactone (24a)

A stirred heterogeneous solution of 1.7 g. (3.4 mmole) 2-[5α-hydroxy-3α(tetrahydropyran-2-yloxy)-2β-(3α-[tetrahydropyran-2-yloxy]-4-2(thienyl)-trans-1-buten-1-yl)cyclopent-1α-yl]acetic acid, γ-lactone (7d) and 300 mg. 5% rhodium on alumina in 35 ml. at absolute methanol is hydrogenated for 90 minutes. The reaction mixture is filtered through filter aid and concentrated (in vacuo) to yield 2-[5α-hydroxy-3α(tetrahydropyran-2-yloxy)-2β-(3α-[tetrahydropyran-2-yloxy]-4-2(thienyl)-but-1-yl)cyclopentan-1α-yl]acetic acid, γ-lactone (24a).

EXAMPLE 15

2-[5α-Hydroxy-3α-(tetrahydropyran-2-yloxy)-2β-(3α-[tetrahydropyran-2-yloxy]-4-(2-thienyl)but-1-yl)cyclopent-1α-yl]acetaldehyde, γ-hemiacetal (25a)

A solution of 1600 mg. (3.2 mmole) 2-[5α-hydroxy-3α-(tetrahydropyran-2-yloxy)-2β-(3α-[tetrahydropyran-2-yloxy]-4-2(thienyl) but-1-yl)cyclopent-1α-yl]acetic acid, γ-lactone (24a) in 15 ml. dry toluene is cooled to −78° in a dry nitrogen atmosphere. To this cooled solution is added 5.0 ml. of 20% diisobutylaluminum hydride in n-hexane (Alfa Inorganics) dropwise at such a rate so that the internal temperature never rises above −65° (3 minutes. After an additional 30 minutes of stirring at −78°, anhydrous methanol is added until gas evolution ceases and the reaction mixture is allowed to warm to room temperature. The reaction mixture is combined with 150 ml. ether, washed with 50% sodium potassium tartrate solution (1 × 50 ml.), dried ($Na_2SO_4$) concentrated, and chromatographed to yield 2-[5α-hydroxy-3α-(tetrahydropyran-2-yloxy)-2β-(3α-[tetrahydropyran-2-yloxy]-4-(2-thienyl)but-1-yl(cyclopent-1-yl]acetaldehyde, γ-hemiacetal (25a).

EXAMPLE 16

9α-Hydroxy-11α,15α-bis-(tetrahydropyran-2-yloxy)-16-(2-thienyl)-cis-5-ω-tetranorprostenoic Acid (22a):

To a solution of 5150 mg. (11.6 mmole) (4-carbohydroxy-n-butyl)triphenylphosphonium bromide in a dry nitrogen atmosphere in 10.1 ml. dry dimethyl sulfoxide is added 10.8 ml. (21.1 mmole) of a 1.96M solution of sodium methylsulfinylmethide in dimethyl sulfoxide. To this red ylide solution is added dropwise a solution of 1300 mg. (2.6 mmole) 2-[5α-hydroxy-3α-(tetrahydropyran-2-yloxy)2β-(3α-[tetrahydropyran-2-yloxy]-4-(2-thienyl)-but-1-yl)cyclopent-1α-yl]acetaldehyde, γhemiacetal (25a) in 7.0 ml. dry dimethyl sulfoxide over a period of 20 minutes. After an additional 2 hours stirring at room temperature, the reaction mixture is poured into ice water. The basic aqueous solution is acidified to pH~3 with 10% aqueous hydrochloric acid. The acid solution is extracted with ethyl acetate (3 × 100 ml.) and the combined organic extracts washed once with water (50 ml.), dried (MgSO$_4$) and evaporated to a solid residue. This solid residue is triturated with ethyl acetate and filtered. The filtrate is purified by column chromatography on silica gel to provide 9α-hydroxy-11α,15α-bis-(tetrahydropyran-2-yloxy)-16-(2-thienyl)-cis-5ω-tetranorprostenoic (22a) acid is collected.

The product obtained above (22a) may be converted to 16-(2-thienyl)-ω-tetranor-13,14-dihydro PGF$_{2α}$ via the process of Example 10.

EXAMPLE 17

9-oxo-11α,15α-bis-(tetrahydropyran-2-yloxy)-16-(2-thienyl)-cis-5-ω-tetranorprostenoic Acid (26a)

To a solution cooled to −10° under nitrogen of 950 mg. (1.68 mmole) 9α-hydroxy-11α,15α-bis-(tetrahydropyran-2-yloxy)-16-(2-thienyl)-cis-5-ω-tetranorprostenoic acid (22a) in 15 ml. reagent grade acetone is added dropwise 0.75 ml. (2 mmole) of Jones' reagent. After 20 minutes at −10°, 0.75 ml. 2-propanol is added and the reaction mixture is allowed to stir an additional 5 minutes at which time it is combined with 100 ml. ethyl acetate, washed with water (3 × 25 ml.), dried (MgSO$_4$) and concentrated to give of 9-oxo-11α,15α-bis-(tetrahydropyran-2-yloxy)-16-(2-thienyl-cis-5-ω-tetranorprostenoic acid (26a).

EXAMPLE 18

9-oxo-11α,15α-dihydroxy-16-(2-thienyl)-cis-5-ω-tetranorprostenoic Acid (27a)

A solution of 800 mg. 9-oxo-11α,15α-bis-(tetrahydropyran-2-yloxy)-16-(2-thienyl)-cis-5-ω-tetranorprostenoic acid (26a) in 7.0 ml. of a 65:35 mixture of glacial acetic acid:water is stirred under nitrogen at 25° for 20 hours and then is concentrated by rotary evaporation. The resultant crude oil is purified by column chromatography to provide the 9-oxo-11α,15α-dihydroxy-16-(2-thienyl)-cis-5-ω-tetranorprostenoic acid (27a).

The product of this example (27a) may be converted to the 16-(2-thienyl)-cis-5-ω-tetranorprostaglandin A$_2$ by the procedure of Example 12.

EXAMPLE 19

9-oxo-11α,15α-dihydroxy-16-(2-thienyl)-ω-tetranorprostanoic Acid (28a)

A heterogeneous solution of 37 mg. (.089 mmole) 9-oxo-1α, 15α-dihydroxy-16-(2-thienyl)-cis-5-trans-13-ω-tetranorprostadienoic acid (11d) and 37 mg. of 5% rhodium on alumina in 3 ml. absolute methanol is hydrogenated (1 atm) at 0° for 2 hours. The reaction mixture is filtered and evaporated to yield 9-oxo-11α,15α-dihydroxy-16-(2-thienyl)-ω-tetranorprostanoic acid (28a).

EXAMPLE 20

9-oxo-11α,15α-dihydroxy-16-(2-thienyl)-trans-13-ω-tetranorprostenoic Acid (29a)

A solution of 50 mg. 9-oxo-11α,15α-dihydroxy-16-(2-thienyl)-cis-5-trans-13-ω-tetranorprostadienoic acid (11a) in 5 ml. of dry tetrahydrofuran is treated with 448 mg. (3.6 mmole) dimethyl isopropyl chlorosilane and 1.0 g. (3.6 mmole) 1,1,3,3-tetramethyl-1,3-diisopropyldisilazane at 25° for 48 hours, evaporated to a residue. The crude residue is then taken up in 6 ml. of a 3:2 mixture of acetone:benzene and 30 mg. of tris (triphenylphosphine) rhodium chloride is added and the resultant solution is hydrogenated for 7 hours at 20-30 psi. The solution is evaporated and the residue dissolved in 2.0 ml. of ethanol then poured into 5 ml. of 0.2M Na$_2$HPO$_4$ buffer. The mixture is extracted with ether, then the aqueous layer is acidified to pH 3 with 10% hydrochloric acid, is stirred for 5 minutes then is extracted with ethyl acetate. The combined organic extracts are washed with water (2 × 10 ml.), dried (MgSO$_4$) and evaporated to yield 9-oxo-11α,15α-dihydroxy-16-(2-thienyl)-trans-13-ω-tetranorprostenoic acid (29a) after silica gel chromatography.

EXAMPLE 21

2-[2β-benzyloxymethyl-3α-(tetrahydropyran-2-yloxy)-5α-hydroxycyclopent-1α-yl]acetaldehyde, γ-hemiacetal To a stirred solution, cooled to −78°, of the 2-[2α-benzyloxymethyl-3α-(tetrahydropyran-2-yloxy)-5α-hydroxycyclopent-1α-yl]acetic acid, γ-lactone in 78.8 ml. of toluene was added 13.4 ml. (10.8 mmoles) of a 0.805M solution of diisobutylaluminum hydride in hexane dropwise. The solution was stirred in the cold under nitrogen for 1.0 hour then was quenched by the dropwise addition of methanol until gas evolution ceased. The quenched mixture was warmed to room temperature, was diluted with ether (79 ml.), was washed with 50% sodium potassium tartrate (3x) and saturated brine (1x), was dried (anhydrous magnesium sulfate), and was concentrated to afford the crude, colorless, oily 2-[2β-benzyloxymethyl-3α-(tetrahydropyran-2-yloxy)-5α-hydroxycyclopent-1α-yl]acetaldehyde, γ-hemiacetal weighing 3.15 g. (92.0% yield). The ir, nmr, and mass spectra of the oil were consistent with the assigned structure.

Spectra:
 ir (CHCl$_3$):
  no carbonyl
 nmr (CDCl$_3$):

| | | | | |
|---|---|---|---|---|
| 7.31 | δ | singlet | 5H | aromatic |
| 5.32–5.75 | δ | broad singlet | 1H | OH |
| 4.50 | δ | singlet | 2H | φCH$_2$—O |
| 4.45–4.98 | δ | multiplet | 2H | O—CH—O |
| 3.44 | δ | quartet J = 9 cps J = 4 cps | 2H | —CH$_2$O—BZ |
| 1.20–4.40 | δ | multiplets | 16H | remaining protons |

EXAMPLE 22

7-[2β-benzyloxymethyl-3α-(tetrahydropyran-2-yloxy)-5α-hydroxycyclopent-1α-yl]-cis-5-heptenoic Acid To a solution of 4.96 g. (11.2 mmoles) of (4-carboxy-n-butyl)triphenylphosphonium bromide in 8.85 ml. of dimethyl sulfoxide was added dropwise 9.73 ml. (21.2 mmoles) of a 2.18 M solution of sodium methylsulfinylmethide in dimethyl sulfoxide. To the resultant red ylide solution was added dropwise over a period of 1.0 hour a solution of 1.57 g. (4.50 mmoles) of the crude hemiacetal prepared in Example 21 in 13.7 ml. of dimethyl sulfoxide. After being stirred for an additional 45 minutes the reaction was poured onto ice-water. The basic aqueous solution was extracted with a 2:1 mixture of ethyl acetate-ether (2 × 60 ml was then covered with ethyl acetate, and was acidified with 1.0 N hydrochloric acid to pH ~3. The aqueous layer was extracted further with ethyl acetate; the combined ethyl acetate extracts were washed with water, were dried (anhydrous magnesium sulfate), and were concentrated to a viscous yellow oil. The crude oil was purified by chromatography on 30 g. of silica gel using ethyl acetate as eluent. After elution of high R$_f$ impurities the desired 7-[2β-benzyloxymethyl-3α-(tetrahydropyran-2-yloxy)-5α-hydroxycyclopent-1α-yl]-cis-5-heptenoic acid was collected weighing 1.75 g. (90.0% yield).

Spectra:
ir (CHCl$_3$):
5.82 μ    acid    carbonyl
nmr (CDCl$_3$):

| | | | |
|---|---|---|---|
| 7.30 δ | singlet | 5H | aromatic |
| 6.44–7.00 δ | broad singlet | 2H | —OH |
| 5.28–5.58 δ | multiplet | 2H | olefinic |
| 4.62–4.79 δ | broad singlet | 1H | —O—CH—O |
| 4.51 δ | singlet | 2H | φ—CH$_2$—O |
| 3.23–4.38 δ | multiplets | 8H | —CH—O & —CH—O |
| 1.22–2.53 δ | multiplets | 16H | remaining protons |

Optical Rotation:
[απ$_D^{25}$] = + 15.1° (C 9.94, HCCl$_3$).

EXAMPLE 23

Methyl 7-[2β-benzyloxymethyl-3α-(tetrahydropyran-2-yloxy)-5α-hydroxycyclopent-1α-yl]cis-5-heptenoate A solution of 1.75 g. (4.06 mmoles) of the chromatographed acid prepared in Example 22 in 17.5 ml. of anhydrous ether was titrated at room temperature with an ethereal diazomethane solution until the yellow color persisted for 5 minutes. The reaction was then decolorized by the dropwise addition of glacial acetic acid. The ethereal solution was then washed with saturated sodium bicarbonate (1x) and saturated brine (1x), was dried (anhydrous magnesium sulfate), and was concentrated to afford the faintly-yellow, oil methyl 7-[2β-benzyloxymethyl-3α-(tetrahydropyran-2-yloxy)-5α-hydroxycyclopent-1α-yl]-cis-5-heptenoate weighing 1.80 g. (99.0% yield).

Spectra:
ir (CHCl$_3$):
5.77 μ    Ester carbonyl
nmr (CDCl$_3$):

| | | | |
|---|---|---|---|
| 7.31 δ | singlet | 5H | aromatic |
| 5.62–5.30 δ | multiplet | 2H | olefinic |
| 4.81–4.63 δ | broad singlet | 1H | —O—CH—O |
| 4.53 δ | singlet | 2H | φ—CH$_2$—O |
| 3.66 δ | singlet | 3H | —O—CH$_3$ |
| 4.42–3.67 δ | multiplets | 9H | —CH$_2$—O & —CH—O |
| 2.55–1.36 δ | multiplets | 12H | remaining protons |

EXAMPLE 24

Methyl 7-[2β-benzyloxymethyl-3α-(tetrahydropyran-2-yloxy)-5α-acetoxycyclopent-1α-yl]-cis-5-heptenoate A mixture of 1.58 g. (3.54 mmoles) of the crude hydroxyester prepared in Example 23, 5.0 ml. of pyridine and 0.736 ml. (7.78 mmoles) of acetic anhydride was stirred under nitrogen at 50° overnight. The mixture was then cooled to room temperature and was diluted with ether (75 ml.). The ethereal solution was washed with water (1x) and with saturated copper sulfate (3x), was dried (anhydrous magnesium sulfate), and was concentrated to afford the colorless, oily methyl 7-[2β-benzyloxymethyl-3α-(tetrahydropyran-2-yloxy)-5α-acetoxycyclopent-1α-yl]-cis-5-heptenoate weighing 1.61 g. (93.5% yield).

Spectra:
ir (CHCl$_3$):
1750 cm$^{-1}$    ester carbonyls
nmr (CDCl$_3$):

| | | | |
|---|---|---|---|
| 7.30 δ | singlet | 5H | aromatic |
| 5.51–5.23 δ | multiplet | 2H | olefinic |
| 5.22–4.91 δ | multiplet | 1H | —CH—O—Ac |
| 4.52 δ | singlet | 2H | φ—CH$_2$—O— |
| 3.63 δ | singlet | 3H | —O—CH$_3$ |
| 4.67–3.20 δ | multiplets | 8H | —O—CH & —O—CH$_2$ |
| 2.06 δ | singlet | 3H | O ‖ —CCH$_3$ |
| 2.55–1.22 δ | multiplets | 16H | remaining protons |

EXAMPLE 25

Methyl 7-[2β-hydroxymethyl-3α-(tetrahydropyran-2-yloxy)-5α-acetoxycyclopent-1α-yl]heptanoate A heterogeneous mixture of 1.53 g. (3.14 mmoles) of the crude acetoxy ester prepared in Example 24, 305 mg. of 5% palladium on carbon, and 15.3 ml. of a 20:1 mixture of absolute ethanol:glacial acetic acid was stirred at room temperature under one atmosphere of hydrogen for 48 hours. The mixture was then filtered through Celite 545 and the filtrate was concentrated to afford the colorless, oily methyl 7-[2β-hydroxymethyl-3α-(tetrahydropyran-2-yloxy)-5α-acetoxycyclopent-1α-yl]heptanoate weighing 1.10 g. (87.5% yield Spectra:
ir (CHCl$_3$):
1750 cm$^{-1}$    ester carbonyls
nmr (CDCl$_3$):

| | | | |
|---|---|---|---|
| 5.23–4.92 δ | multiplet | 1H | —CH—OAc |
| 4.83–4.46 δ | multiplet | 1H | —O—CH—O |
| 3.65 δ | singlet | 3H | —O—CH$_3$ |
| 4.32–3.18 δ | multiplets | 7H | —O—CH & —O—CH$_2$— |
| 3.06–2.70 δ | broad singlet | 3H | O ‖ —CCH$_3$ |
| 2.58–1.00 δ | multiplets | 20H | remaining protons |

EXAMPLE 26

Methyl 7-[2β-formyl-3α-(tetrahydropyran-2-yloxy)-5α-acetoxycyclopent-1α-yl]heptanoate To a mechanically stirred solution of 3.37 ml. (41.7 mmoles) of pyridine in 50 ml. of methylene chloride cooled to 10° to 15° under nitrogen was added portionwise over a period of 30 minutes 1.89 g. (18.9 mmoles) of chromium trioxide. The dark burgundy solution was then let warm to room temperature then was cooled to 0°. To the solution was added a solution of 0.947 g. (2.37 mmole) of the crude alcohol prepared in Example 25 in 7.0 ml. of methylene chloride with the concomitant formation of a dense black precipitate. The suspension was stirred in the cold for 15 minutes then 7.21 g. (52.2 mmoles) of finely ground sodium bisulfate monohydrate was added. After being stirred for 10 minutes 6.25 g. (52.2 mmoles) of anhydrous magnesium sulfate was added. After being stirred for 5 minutes the dark suspension was filtered through a pad of Celite, was washed with methylene chloride, then was concentrated by rotary evaporation (bath <10°) to afford the crude, dark brown, oily methyl 7-[2β-formyl-3α-(tetrahydropyran-2-yloxy)-5α-acetoxycyclopent-1α-yl]heptanoate which was used without purification.

EXAMPLE 27

Methyl 9α-acetoxy-11α-(tetrahydropyran-2-yloxy)-15-oxo-trans-13-16-(2-thienyl)-ω-tetranorprostenoate To a suspension of 137 mg. (3.25 mmoles) of a 57.0% dispersion of sodium hydride in mineral oil in 30 ml. of tetrahydrofuran was added 885 mg. (3.55 mmoles) of dimethyl-2-oxo-3-(2-thienyl)propylphosphonate. The mixture was stirred at room temperature for 0.5 hour under nitrogen. To this suspension was added a solution of 1.30 g. (3.25 mmoles) of the crude aldehyde prepared in Example 25 in 10 ml. of tetrahydrofuran. The resultant slightly turbid, brown solution was stirred at room temperature for 2.0 hours under nitrogen. The reaction was then quenched by the addition of glacial acid to pH~5 and was concentrated by rotary evaporation. The crude product was purified by column chromatography on silica gel using mixture of benzene:ether as eluents to afford the desired methyl 9α-acetoxy-11α-(tetrahydropyran-2-yloxy)-15-oxo-trans-13-16-(3-thienyl)-ω-tetranorprostenoate as a viscous yellow oil weighing 941 mg.

EXAMPLE 28

Methyl 9α-acetoxy-11α-(tetrahydropyran-2-yloxy)-15-hydroxy-trans-13-16-(2-thienyl)-ω-tetranorprostenoate To a solution, cooled to −78°, of 0.941 g. (1.81 mmoles) of the enone prepared in Example 27 in 25 ml. of tetrahydrofuran was added dropwise 1.81 ml. (1.81 mmoles) of a 1:0M lithium triethylborohydride solution in tetrahydrofuran. After being stirred in the cold under nitrogen for 25 minutes the reaction was quenched by the addition of 1 ml. of a 9:1 mixture of water:acetic acid. The quenched heterogeneous solution was warmed to room temperature and concentrated. The residue was dissolved in ethyl acetate, the organic layer was washed with water and saturated sodium bicarbonate, was dried (MgSO$_4$), and concentrated. The crude product was purified by silica gel chromatography using mixtures of benzene:ether as eluents which afforded methyl 9α-acetoxy-11α-(tetrahydropyran-2-yloxy)-15β-hydroxy-trans-13-16(2-thienyl)-ω-tetranor prostenoate weighing 257 mg then after mixed fractions methyl 9α-acetoxy-11α-(tetrahydropyran-2-yloxy)-15α-hydroxy-trans-13-16-(2-thienyl)-ω-tetranorprostenoate weighing 455 mg.

EXAMPLE 29

Methyl-9α-acetoxy-11α,15β-dihydroxy-trans-13-16-(2-thienyl)-ω-tetranorprostenoate and methyl 9α-acetoxy-11α,15α-dihydroxy-ω-trans-13-16-(2-thienyl)-ω-tetranorprostenoate A solution of 1.60 g. (2.16 mmoles) of the crude THP ether prepared in Example 28 in 10.7 ml. of a 65:35 mixture of acetic acid:water is stirred at 40 ± 2° under nitrogen for 2.5 hours. The reaction mixture is then concentrated to afford the crude epimeric diol mixture. The crude product is purified by column chromatography on silica gel to provide the desired methyl-9α-acetoxy-11α,15β-dihydroxy-trans-13-16-(2-thienyl)-ω-tetranorprostenoate and the epimeric methyl 9α-acetoxy-11α,15α-dihydroxy-trans-13-16-(2-thienyl)-ω-tetranorprostenoate.

EXAMPLE 30

Methyl 9α-acetoxy-11α,15α-bis-(tetrahydropyran-2-yloxy)-trans-13-16-(2-thienyl)-ω-tetranorprostenoate A mixture of 0.413 g. (0.790 mmole) of the chromatographed more polar epimer of Example 28, 0.22 ml. (2.40 mmoles) of dihydropyran, 8 ml. of methylene chloride, and 1 crystal of p-toluenesulfonic acid monohydrate was stirred at room temperature under nitrogen for 30 minutes. The reaction mixture was then diluted with ether, is washed with saturated aqueous sodium bicarbonate, was dried (anhydrous magnesium sulfate), and was concentrated to give the desired methyl 9α-acetoxy-11α,15α-bis-(tetrahydropyran-2-yloxy)-trans-13-16-(2-thienyl)-ω-tetranorprostenoate as a yellow oil weighing 517 mg. (>100% yield).

EXAMPLE 31

9α,11α,15α-trihydroxy-trans-13-16-(2-thienyl)-ω-tetranorprostenoic Acid

A mixture of 65 mg. (0.15 mmoles) of the chromatographed diol prepared in Example 29, 0.45 ml. (0.45 mmole) of 1.0 N aqueous sodium hydroxide, 0.45 ml. of tetrahydrofuran, and 0.45 ml. of absolute methanol is stirred under nitrogen at room temperature for 1.5 hours. The solution is then acidified by the addition of 0.45 ml. of 1.0 N aqueous hydrochloric acid (pH of acidified solution was ca. 5). The acidified solution is extracted with ethyl acetate (4 × 2 ml.). The combined extracts are dried (anhydrous magnesium sulfate) and concentrated to afford the desired 9α,11α,15α-trihydroxy-trans-13-16-(2-thienyl)-ω-tetranorprostenoic acid.

EXAMPLE 32

9α-hydroxy-11α,15α-bis-(tetrahydropyran-2-yloxy)-trans-13-16-(2-thienyl)-ω-tetranorprostenoic Acid A homogeneous solution of 5.7 mg (0.790 mmole) of the crude bis-THP ester prepared in Example 30, 2.37 ml (2.37 mmoles) of the 1.0N aqueous sodium hydroxide solution, 2.0 ml of methanol, and 2.5 ml of tetrahydrofuran was stirred under nitrogen for 2 hours. The reaction was then quenched by the addition of 2.37 ml of a 1.0N aqueous hydrochloric acid solution. The quenched solution was diluted with ethyl acetate. The organic layer was dried (anhydrous magnesium sulfate) and concentrated to afford the crude product. The crude product was purified by column chromatography on Baker "Analyzed" silica gel (60-200 mesh) using mixtures of benzene: ether as eluents to provide the 9α-hydroxy-11α,15α-bis-(tetrahydropyran-2-yloxy)-trans-13-16-(2-thienyl)-ω-tetranorprostenoic acid as a yellow oil weighing 414 mg (95.4% yield).

EXAMPLE 33

9-oxo-11α,15α-bis-(tetrahydropyran-2-yloxy)-13-trans-16-(2-thienyl)-ω-tetranorprostenoic Acid To a solution, cooled under nitrogen to −15° to −20°, of 414 mg (0.751 mmole) of the chromatographed acid prepared in Example 32 in 8.0 ml of acetone was added dropwise 0.310 ml (0.27 mmole) of Jones' reagent. The reaction was stirred in the cold for 20 minutes then was quenched by the addition of 0.31 ml of isopropanol. The quenched reaction was stirred in the cold for 5 minutes then was diluted with ethyl acetate. The organic solution was washed with water (2x) and saturated brine (1x), was dried (anhydrous magnesium sulfate), and was concentrated to afford the desired 9-oxo-11α,15α-bis-(tetrahydropyran-2-yloxy)-13-trans-16-(2-thienyl)-ω-tetranorprostenoic acid as a yellow oil weighing 367 mg (89.0% yield).

EXAMPLE 34

9-oxo-11α,15α-dihydroxy-13-trans-16-(2-thienyl)-ω-tetranorprostenoic Acid

A homogeneous solution of 367 mg (0.670 mmole) of the crude THP ether of Example 33 in 10 ml of a 65:35 mixture of acetic acid:water was stirred under nitrogen at room temperature for 17.5 hours. The reaction was concentrated by rotary evaporation followed by oil pump. The crude brown product was purified by column chromatography on silica gel (Mallinckrodt CC-7) using mixtures of chloroform: ethyl acetate as eluents to provide the desired 9-oxo-11α,15α-dihydroxy-13-trans-16-(2-thienyl)-ω-tetranorprostenoic acid as a crystalline solid weighing 144 mg (56.7% yield) and melting at 63°–65° from ether: cyclohexane.

EXAMPLE 35

Dimethyl 2-Oxo-4-(2-thienyl)butylphosphonate (2b)

A solution of 11.6 g (94 mmoles) dimethyl methylphosphonate (Aldrich) in 130 ml. dry tetrahydrofuran was cooled to −78° in a dry nitrogen atmosphere. To the stirred phosphonate solution was added 43 ml of 2.26 M n-butyllithium in hexane solution (Alfa Inorganics, Inc.) dropwise over a period of 18 minutes at such a rate that the reaction temperature never rose above −65°. After an additional 5 minutes stirring at −78°, 8.0 g. (47 mmole) methyl 3-(2-thienyl)propionate was added dropwise at a rate that kept the reaction temperature less than −70° (20 minutes). After 3.5 hours at −78°, the reaction mixture was allowed to warm to ambient temperature, neutralized with 5 ml. acetic acid and rotary evaporated to a white gel. The gelatinous material was taken up in 75 ml. water, the aqueous phase extracted with 100 ml. portions of chloroform (3x), the combined organic extracts were backwashed (50 cc $H_2O$), dried ($MgSO_4$), and concentrated (water aspirator) to a crude residue and distilled, b.p. 156° (0.2mm) to give 9.7 g. dimethyl 2-oxo-4-(2-thienyl)-butylphosphonate.

The nmr spectrum (CDCl) showed a doublet centered at 3.75δ(J=11.5 c.ps.,6H) for

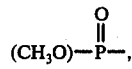

a triplet centered at 3.11δ(4H) for —$CH_2$—$CH_2$—, a doublet centered at 3.14δ(J=23 cps, 2H)

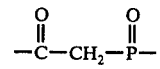

and a multiplet 6.7–7.4δ (3H) for thienyl ring protons

In the same manner dimethyl 2-oxo-4-(3-thienyl) butyphosphonate may be prepared from methyl 3-(3-thienyl) propionate. This is also a suitable starting material in the preparation of 17-(3-thienyl)-ω-trisnorprostaglandins of the A, E and F series via examples 3–20. In the same manner starting materials suitable for conversion to 18, 19 or 20 α or β-thienyl substituted prostaglandins by the procedure of Examples 1–20 can be synthesized from the appropriate esters.

EXAMPLE 36

2-[3α-p-Phenylbenzoyloxy-5α-hydroxy-2β-(3oxo-5-(2-thienyl)-trans-1-penten-1-yl)-cyclopent-1α-yl]Acetic Acid, γ-lactone (3b)

Dimethyl 2-oxo-4-(2-thienyl)butylphosphate (2b) (2.81g, 7.5 mmole) in 100 ml anhydrous ether was treated with 3.32 ml. (7.5 mmole) 2.26 M n-butyllithium in n-hexane (Alfa Inorganics, Inc.) in a dry nitrogen atmosphere at room temperature. After 5 min. of stirring, an additional 200 ml. of anhydrous ether was added followed by 2.0 g. (5.7 mmole) 2-[3α-p-phenylbenzoyloxy-5α-hydroxy-2β-formylcyclopentan-1α-yl]acetic acid, γ-lactone in one portion and 20 ml. anhydrous ether. After 35 minutes the reaction mixture was quenched with 0.5 ml. glacial acetic acid and washed with 100 ml. saturated sodium bicarbonate solution (4x), 100 ml water (2x), 100 ml. saturated brine (1x), dried ($MgSO_4$) and evaporated to yield an oil which crystallized from $CH_2Cl_2$-hexane to give 2.4 g. 2-[3α-p-phenylbenzoyloxy-5α-hydroxy-2β-(3-oxo-5-(2-thienyl)-trans-1-penten-1-yl)cyclopent-1α-yl]acetic acid, γ-lactone (3b) m.p. 121°–123°.

The ir spectrum (KBr) of the product exhibited adsorbtion bands at 1776 cm$^{-1}$ (strong), 1710 cm$^{-1}$ (strong), 1676 cm$^{-1}$ medium and 1636 cm$^{-1}$.

The productt of this example (3b) may be converted to 13,14 dihydro-17-(2-thienyl)-ω-trisnorprostaglandins of the A, E or F series through the procedures of examples 10, 12–13 and 15–18. The product (3b) may also be converted to 15-lower alkyl-17-(2-thienyl)-ω-trisnorprostaglandins of the A, E or F series by the procedures of examples 4–20. 15-lower-alkyl-13,14 dihydro-17-(2-thienyl)-ω-trisnorprostaglandins of the A, E or F series may be obtained from (3b) by the procedures of examples 10–13 and 15–18.

EXAMPLE 37

2-[3α-p-Phenylbenzoyloxy-5α-hydroxy-2β-(3α-hydroxy-5-(2-thienyl)-trans-1-penten-1-yl)cyclopent-1α-yl]acetic Acid, γ-lactone (4b) and 2[3α-p-Phenylbenzoyloxy-5α-hydroxy-2β-(3β-hydroxy-5-(2-thienyl)-trans-1-penten-1-yl)cyclopent-1α-yl]acetic Acid, γ-lactone-(5b)

To a solution of 4.53 g (9.3 mmole) 2-[3α-p-phenyl-benzoyloxy-5α-hydroxy-2β-(3-oxo-5-(2-thienyl)-trans-1-penten-1-yl)cyclopent-1α-yl]acetic acid, γ-lactone (3b) in 28 ml dry 1,2-dimethoxyethane in a dry nitrogen atmosphere at ambient temperature was added dropwise 9.3 ml of a 0.5 M zinc borohydride solution. After stirring at room temperature for 45 minutes, a saturated sodium bitartrate solution was added dropwise until hydrogen evolution ceased. The reaction mixture was allowed to stir for 5 minutes at which time 300 ml dry methylene chloride was added. After drying (MgSO$_4$) and concentrating (water aspirator), the resultant semisolid was purified by column chromatography on silica gel (Baker "Analyzed" Reagent 60-200 mesh) using ether as eluent. After elution of less polar impurities, a fraction containing 1.44 g 2-[3α-p-phenylbenzoyloxy-5α-hydroxy-2β-(3α-hydroxy-5-(2-thienyl)-trans-1-penten-1-yl)cyclopent-1α-yl]acetic acid, γ-lactone (4b), a 200 mg fraction of mixed (4b) and (5b) and finally a fraction (1.72 g) of 2-[3α-p-phenylbenzoyloxy-5α-hydroxy-2β-(3β-hydroxy-5-(2-thienyl)-trans-1-penten-1-yl) cyclopent-1α-yl]acetic acid, γ-lactone (5b) was obtained.

The ir spectrum (CHCl$_3$) of 4b and 5b had strong carbonyl adsorbtions at 1765 and 1709 cm$^{-1}$ and an adsorbtion at 970 cm$^{-1}$ for the trans double bond.

EXAMPLE 38

2-[3α,5α-Dihydroxy-2β-(3α-hydroxy-5-(2-thienyl)-trans-penten-1-yl)cyclopent-1α-yl]acetic Acid, γ-lactone (6b)

A heterogeneous mixture of 1.44 g (2.95 mmole) of 2-[3α-p-phenylbenzoyloxy-5α-hydroxy-2β-(3α-hydroxy-5-(2-thienyl)-trans-1-penten-1-yl)cyclopent-1α-yl]acetic acid, γ-lactone (4b), 16 ml. of absolute methanol and 75 mg of finely powdered, anhydrous potassium carbonate was stirred at room temperature overnight, then cooled to 0°. To the cooled solution was added 1.0 ml (1.0 mmole) of 1.0N aqueous hydrochloric acid. After stirring at 0° for an additional 10 minutes, 10 ml. of water was added with concomitant formation of methyl p-phenylbenzoate which was collected by filtration. The filtrate was saturated with solid sodium chloride, extracted with ethyl acetate (4 × 20 ml.), the combined organic extracts were washed with saturated sodium bicarbonate (10 ml.), dried (MgSO$_4$) and concentrated to give 839 mg (92%) of crystalline, 2-[3α,5α-dihydroxy-2β-(3α-hydroxy-5-(2-(thienyl)-trans-1-penten-1-yl)cyclopent-1α-yl]acetic acid, γ-lactone (6b), mp. 98°-100°.

The ir spectrum (CHCl$_3$) exhibited a strong adsorption at 1765 cm$^{-1}$ for the lactone carbonyl and medium adsorption at 970 cm$^{-1}$ for the trans-double bond.

EXAMPLE 39

2-[3α,5α-Dihydroxy-2β-(3β-hydroxy-5-(2-thienyl)-trans-1-penten-1-yl)cyclopent-1α-yl]acetic acid, γ-lactone (6'b)

A heterogeneous mixture of 1.72 g. (3.52 m mole) of 2-[3α-p-phenylbenzoyloxy-5α-hydroxy-2β-(3β-hydroxy-5-(2-thienyl)-trans-1-penten-1-yl)cyclopent-1α-yl]acetic acid, γ-lactone (4b), 20 ml. of absolute methanol and 90 mg. of finely powdered, anhydrous potassium carbonate was stirred at room temperature for 18 hours, than cooled to 0°. To the cooled solution was added 1.0 ml (2.0 mmole) of 1.0N aqueous hydrochloric acid. After stirring at 0° for an additional 10 minutes, 15 ml. of water was added with concomitant formation of methyl p-phenylbenzoate which was collected by filtration. The filtrate was saturated with solid sodium chloride, extracted with ethyl acetate (4 × 10 ml), the combine organic extracts were washed with saturated sodium bicarbonate (10 ml.) dried (MgSO$_4$) and concentrated to give 967 mg. (90%) of viscous, oily 2-[(3α,5α-dihydroxy-2β-(3β-hydroxy-5-(2-thienyl) trans-1-penten-1-yl)cyclopent-1α-yl]acetic acid, γ-lactone (6'b)

The ir spectrum (CHCl$_3$) exhibiited a strong adsorption at 1768 cm$^{-1}$ for the lactone carbonyl and medium adsoprtion at 968cm$^{-1}$ for the trans-double bond.

EXAMPLE 40

2-[5α-Hydroxy-3α-(tetrahydropyran-2-yloxy)-2β-(3α-{tetrahydropyran-2-yloxy}-5-(2-thienyl)-trans-1-penten-1-yl)cyclopent-1α-yl]acetic Acid, γ-lactone (7b)

To a solution of 839 mg (2.72 mmole) 2-[3α,5α-dihydroxy-2β-(3α-hydroxy-5-(2-thienyl)-trans-1-penten-1-yl) cyclopent-1α-yl]acetic acid, γ-lactone (6b) in 15 ml anhydrous methylene chloride and 0.75 of 2,3-dihydropyran at 0° in a dry nitrogen atmosphere was added 9 mg p-toluenesulfonic acid monohydrate. After stirring for 15 minutes, the reaction mixture was combined with 200 ml ether, the ether solution washed with saturated sodium bicarbonate (1 × 25 ml) and then saturated brine (1 × 25 ml), dried (MgSO$_4$) and concentrated to yield 1.28 (>100%) crude 2-[(5α-hydroxy-3α-(tetrahydropyran-2-yloxy)-2β-(3α-{tetrahydropyran-2-yloxy}-5-(2-thienyl)-trans-1-penten-1-yl)cyclopent-1α-yl]acetic acid, γ-lactone (7b).

The ir (CHCl$_3$) spectrum has a strong adsorbtion at 965 cm$^{-1}$ for the trans-double bond.

The product of this example (7b) may be converted to 13,14-dihydro-17-(2-thienyl)-ω-trisnorprostaglandins of the A, E or F series through the procedures of examples 10, 12, 14–18.

EXAMPLE 41

2-[5α-Hydroxy-3α-(tetrahydropyran-2-yloxy)-2β-(3β-(tetrahydropyran-2-yloxy)-5-(2-thienyl)-trans-1-penten-1-yl)cyclopent-1α-yl]acetic Acid, γ-lactone (7'b)

To a solution of 967 mg. (3.14 m mole) 2-[3α,5α-dihydroxy-2β-(3β-hydroxy-5-(2-thienyl-trans-1-penten-1-yl)cyclopent-1α-yl]acetic Acid, γ-lactone (6'b) in 10 ml. anhydrous methylene chloride and 0.85 ml. of 2,3-dihydropyran at 0° in a dry nitrogen atmosphere was added 10 mg. p-toluenesulfonic acid monohydrate. After stirring for 15 minutes, the reaction mixture was combined with 100 ml. ether, the ether solution washed with saturated sodium bicarbonate (1 × 15 ml), then saturated brine (1 × 15 ml.), dried (MgSO$_4$) and concentrated to yield 1.47 g. (>100%) 2-[5α-hydroxy-3α(tetrahydropyran-2-yloxy)-62-(3β-(tetrahydropyran-2-yloxy)-5-(2-thienyl)-trans-1-penten-1-yl)cyclopent-1α-yl]acetic acid, γ-lactone (7'b), which after crystallization from etherhexane had mp. 80°-82°.

The ir (CHCl$_3$) spectrum has a strong adsorbtion at 960 cm$^{-1}$ for the trans-double bond.

EXAMPLE 42

2-[(5α-Hydroxy-3α-(tetrahydropyran-2-yloxy)-2β-(3α-{tetrahydropyran-2-yloxy}-5-(2-thienyl)-trans-1-penten-yl)cyclopent-1α-yl]acetaldehyde, γ-hemiacetal (8b)

A solution of 1.28 g (2.7 mmole) of 2-[5α-hydroxy-3α-(tetrahydropyran-2-yloxy)-2β-(3α-{tetrahydropyran-2-yloxy}-5-(2-thienyl)-trans-1-penten-1yl)cyclopent-1α-yl]acetic acid, γ-lactone (7b) in 13 ml dry toluene was cooled to −78° in dry nitrogen atmosphere. To this cooled solution was added 3.7 ml of 0.8 M diisobutylaluminum hydride in n-hexane (Alfa Inorganics) dropwise at such a rate so that the internal temperature never rose above −65° (15 minutes). After an additional 45 minutes of stirring at −78°, anhydrous methanol was added until gas evolution ceased and the reaction mixture was allowed to warm to room temperature. The reaction mixture was combined with 150 ml ether, washed with 50% sodium potassium tartrate solution (4 × 20 ml), dried (Na$_2$SO$_4$) and concentrated to a quantitative yield of oily 2-[5α-hydroxy-3α-(tetrahydropyran-2-yloxy)-2β-(3α-{tetrahydropyran-2-yloxy}-5-(2-thienyl)-trans-1-penten-1-yl)cyclopent-1-yl]acetaldehyde, γ-hemiacetal (8b).

EXAMPLE 43

2-[5α-Hydroxy-3α-(tetrahydropyran-2-yloxy)-2β-(3β-(tetrahydropyran-2-yloxy)-5-(2-thienyl)-trans-1-penten-1-yl)cyclopent-1α-yl]acetaldehyde, γ-hemiacetal (8'b)

A solution of 1.47 g (3.1 m mole) 2-[5α-hydroxy-3α-(tetrahydropyran-2-yloxy)-2β-(3β-(tetrahydropyran-2-yloxy)-5-(2-thienyl-trans-1-penten-1-yl)cyclopent-1α-yl] acetic acid, γ-lactone (7'b) in 15 ml. dry toluene was cooled to −78°, in a day nitrogen atmosphere. To this cooled solution was added 4.25 ml. of 0.8M diisobutylaluminum hydride in n-hexane (Alfa Inorganics) dropwise at such a rate so that the internal temperature never rose above −65° (15 minutes). After an additional 45 minutes of stirring at −78°, anhydrous methanol was added until gas evolution ceased and the reaction mixture was allowed to warm to room temperature The reaction mixture was combined with 100 ml. ether, washed with 50% sodium potassium tartrate solution (4 × 20 ml), dried (Na$_2$SO$_4$) and concentrated to yield 1.38 g. 2-[5α-hydroxy-3α-(tetrahydropyran-2-yloxy)-2β-(3β-tetrahydropyran-2-yloxy-5-(2-thienyl)-trans-1-penten-1-yl)cyclopent-1α-yl]acetaldehyde, γ-hemiacetal (8'b).

EXAMPLE 44

9α-Hydroxy-11α,15α-bis-(tetrahydropyran-2-yloxy)-17-(2-thienyl)-cis-5-trans-13-ω-trisnor prostadienoic Acid (9b)

To a solution of 1.8 g (4.04 mmole) (4-carbohydroxy-n-butyl)triphenylphosphonium bromide in a dry nitrogen atmosphere in 8.0 ml dry dimethyl sulfoxide was added 3.5 ml (7.8 mmole) of a 2.2M solution of sodium methylsulfinylmethide in dimethyl sulfoxide. To this red ylide solution was added dropwise a solution of 717 mg (1.5 mmole) 2-[5α-hydroxy-3α-(tetrahydropyran-2-yloxy)-2β-(3α-{tetrahydropyran-2-yloxy}-5-(2-thienyl)-trans-1-penten-1-yl)cyclopent-1α-yl]acetaldehyde, γ-hemiacetal (8b) in 5.0 ml dry dimethyl sulfoxide over a period of 20 minutes. After an additional 2 hours stirring at room temperature, the reaction mixture was poured into ice water. The basic aqueous solution was washed twice with ethyl acetate (20 ml.) and acidified to pH 3 with 10% aqueous hydrochloric acid. The acidic solution was extracted with ethyl acetate (3 × 20 ml) and the combined organic extracts washed once with water (10 ml.), dried (MgSO$_4$) and evaporated to a solid residue. This solid residue was triturated with ethyl acetate and filtered. The filtrate was purified by column chromatography on silica gel (Baker "Analyzed" Reagent 60–200 mesh) using ethyl acetate as eluent. After removal of high R$_f$ impurities, 260 mg of 9α-hydroxy-11α,15α-bis-(tetrahydropyran-2-yloxy)-17-(2-thienyl)-cis-5-trans-13-ω-trisnor prostadienoic acid (9b) was collected.

The product of this example (9b) can be converted to 17-(2-thienyl)-ω-trisnorprostaglandins of the F series (F$_{2α}$, F$_{1α}$, F$_{0α}$) via the procedures of examples 10, 19 and 20.

EXAMPLE 45

9α-Hydroxy-11α,15β-bis-(tetrahydropyran-2-yloxy)-17-(2-thienyl)cis-5-trans-13-ω-trisnor prostadienoic acid (9'b)

To a solution of 1.8 g (4.05 mmole) (4-carbohydroxy-n-butyl)triphenylphosphonium bromide in a dry nitrogen atmosphere in 5.0 ml dry dimethyl sulfoxide was added 3.2 ml (7.0 mmole) of a 2.2M solution of sodium methylsufinylmethide in dimethyl sulfoxide. To this red ylide solution was added dropwise a solution of 717 mg (1.34 mmole) 2-[5α-hydroxy-3α-(tetrahydropyran-2-yloxy)-2β-(3α-{tetrahydropyran-2-yloxy}-5-(2-thienyl)-trans-1-penten-1-yl)cyclopent-1α-yl]acetaldehyde, γ-hemiacetal (8'b) in 5.0 ml dry dimethyl sulfoxide over a period of 20 minutes. After an additional 2 hours stirring at room temperature, the reaction mixture was poured into ice water. The basic aqueous solution was washed twice with ethyl acetate (20 ml.) and acidified to pH 23 with 10% aqueous hydrochloric acid. The acidic solution was extracted with ethyl acetate (3 × 20 ml) and the combined organic extracts washed once with water (10 ml.), dried (MgSO$_4$) and evaporated to a solid residue. This solid residue was triturated with ethyl acetate and filtered. The filtrate was purified by column chromatography on silica gel (Baker "Analyzed" Reagent 60–200 mesh) using ethyl acetate as eluent. After removal of high R$_f$ impurities, 740 mg of 9α-hydroxy-11α,15β-bis-(tetrahydropyran-2-yloxy)-17-(2-thienyl)-cis-5-trans-13-ω-trisnor prostadienoic acid (9'b) was collected.

EXAMPLE 46

9-Oxo-11α-15α-bis-(tetrahydropyran-2-yloxy)-17-(2-thienyl)-cis-5-trans-13-ω-trisnor prostadienoic Acid (10b)

To a solution cooled to −10° under nitrogen of 250 mg (0.445 mmole) 9α-hydroxy-11α,15α-bis-(tetrahydropyran-2-yloxy)-17-(2-thienyl)-cis-5-trans-13-ω-trisnor prostadienoic acid (9b) in 10 ml.reagent grade acetone was added dropwise 0.18 ml. (.487 mmole) of Jones' regent. After 20 minutes at −10°, 0.2 ml. 2-propanol was added and the reaction mixture was allowed to stir an additional 5 minutes at which time it was combined with 75 ml. ethyl acetate, washed with (3 × 10 ml.), dried (MgSO$_4$) and concentrated to give 240 mg. of 9-oxo-11α,15α-bis-(tetrahydropyran-2-yloxy)-17-(2-thienyl)-cis-5-trans-13-ω-trisnor prostadienoic acid (10b).

EXAMPLE 47

9-Oxo-11α,15β-bis-(tetrahydropyran-2-yloxy)-17-(2-thienyl)-cis-5-trans-13-ω-trisnor prostadienoic acid (10'b)

To a solution cooled to −10° under nitrogen of 640 mg (1.14 mmole) 9α-hydroxy-11α,15β-bis-(tetrahydropyran-2-yloxy)-17-(2-thienyl)-cis-5-trans-13-ω-trisnor prostadienoic acid (9'b) in 9.2 ml. reagent grade acetone was added dropwise to 0.502 ml. (1.25 mmole) of Jones' reagent. After 20 minutes at −10°, 0.5ml 2-propanol was added and the reaction mixture was allowed to stir an additional 5 minutes, at which time it was combined with 75 ml. ethyl acetate, washed with water (3 × 10 ml.) dried (MgSO$_4$) and concentrated to give 500 mg. of 9-oxo-11α,15β-bis-(tetrahydropyran-2-yloxy)-17-(2-thienyl)-cis-5-trans-13-ω-trisnor prostadienoic acid (10′b).

EXAMPLE 48

9-Oxo-11α,15α-dihydroxy-17-(2-thienyl)-cis-5-trans-13-ω-trisnor prostadienoic Acid (11b)

A solution of 240 mg. (0.334 mmole) 9-oxo-11α,15α-bis-tetrahydropyran-2-yloxy)-17-(2-thienyl)-cis-5-trans-13-ω-trisnor prostadienoic acid (10b) in 3.0 ml. of a 65:35 mixture of glacial acetic acid:water was stirred under nitrogen at 25° for 18 hours and then was concentrated by rotary evaporation. The resultant crude oil was purified by column chromatography on silica gel (Mallinckrodt CC-4 100-200 mesh) using ethyl acetate as eluent. After elution of less polar impurities, the oily 9-oxo-11α,15α-dihydroxy-17-(2thienyl)-cis-5-trans-13-ω-trisnor prostadienoic acid (11b) weighing 100 mg. was collected.

The product of this example (11b) can be converted to 17-(2-thienyl)-ω-trisnorprostaglandin $E_1$, $E_0$, $A_2$, $A_1$ and $A_0$ via the procedures of examples 19, 20, and 12. Biological Activity: Guinea pig uterus 33; rat uterus 50; histamine aerosol test 0; dog blood pressure 10.

EXAMPLE 49

9-Oxo-11α,15β-dihydroxy-17-(2-thienyl)-cis-5-trans-13-ω-trisnor-prostadienoic Acid (11′b)

A solution of 500 mg. (0.893 mmole) 9-oxo-11α,15β-bis-tetrahydropyran-2-yloxy)-17-(2-thienyl)-cis-5-trans-13-ω-tetranorprostadienoic acid (10′b) in 7.0 ml. of a 65:35 mixture of glacial acetic acid:water was stirred under nitrogen at 25° for 18 hours and then was concentrated by rotary evaporation. The resultant crude oil was purified by column chromatography on silica gel (Mallinckrodt CC-4 100-200 mesh) using ethyl acetate as eluent. After elution of less polar impurities, the semisolid 9-oxo-11α,15β-dihydroxy-17-(2-thienyl)-cis-5-trans-13-ω-trisnorprostadienoic acid (11′b) weighing 215 mg was collected.

EXAMPLE 50

Dimethyl 2-Oxo-4-(2-furyl)butylphosphonate (2C)

A solution of 25 g (0.21 mole) dimethyl methylphosphonate (Aldrich) in 300 ml dry tetrahydrofuran was cooled to −78° in a dry nitrogen atmosphere. To the stirred phosphonate solution was added 80 ml of 2.67 M n-butyllithium in hexane solution (Alfa Inorganics, Inc.) dropwise over a period of 18 minutes at such a rate that the reaction temperature never rose above −65°. After an additional 5 minutes stirring at −78°, 16.0 g (.104 mole) methyl 3-(2-furyl)propionate was added dropwise at a rate that kept the reaction temperature less than −70° (20 minutes). After 3.5 hours at −78° the reaction mixture was allowed to warm to ambient temperature, neutralized with 6 ml acetic acid and rotary evaporated to a white gel. The gelatinous material was taken up in 75 ml water, the aqueous phase extracted with 100 ml portions of chloroform (3x), the combined organic extracts were backwashed (50 cc H₂O), dried (MgSO₄), and concentrated (water aspirator) to a crude residue and distilled, b.p. 148°-50° (0.5 mm) to give 8.4 g dimethyl 2-oxo-4-(2-furyl)butylphosphonate (2C).

The nmr spectrum (CDCl₃) showed a doublet centered at 3.73δ (J = 11.5 cps, 6H) for

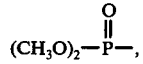

a singlet centered at 2.95δ(2H) for CH₂-CH₂—, a doublet centered at 3.12 δ(J = 23 cps, 2H)

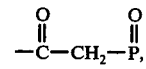

and multiplets at 5.96, 6.23 and 7.23δ (1H each) for furan ring protons.

In a manner similar to the above, dimethyl 2-oxo-4-(3-furyl)butylphosphonate may be obtained by substituting methyl 3-(3-furyl) propionate for methyl 3-(2-furyl) propionate in the above example. This compound is a suitable starting material for the synthesis of 17-(3-furyl)-ω-trisnorprostaglandins of the A, E or F series by the procedures of examples 51-59. In the same manner the dimethyl 2-oxo-2(3-furyl)ethyl phosphonate was prepared BP 140° C. (0.2 mm). This is a suitable starting material for the preparation of 15-(3-furyl)-ω-pentanorprostaglandins of the A, E or F series by the procedure of examples 51-59.

In the same manner the dimethyl-2-oxo-2α-thienyl ethyl phosphonate can be prepared. This is a suitable starting material for the synthesis of 15α-thienyl-ω-pentanorprostaglandins of the A, E or F series by the procedure of examples 36-49.

In a similar manner dimethyl 2-oxo-3(α-furyl)propyl phosphonate, dimethyl-2-oxo-5-(α-furyl)pentylphosphonate, dimethyl-2-oxo-6-(α-furyl)-hexylphosphonate and dimethyl-2-oxo-7-(α-furyl)-heptylphosphonate may be prepared from the appropriate starting materials. These are suitable starting materials for the preparation of the 16, 18, 19 and 20 α-furyl substituted prostaglandin of this invention by the procedure of examples 51-59. The β-furyl derivatives are prepared in the same manner as the α-furyl derivatives from the appropriate starting materials.

EXAMPLE 51

2-[3α-p-Phenylbenzoyloxy-5α-hydroxy-2β-(3-oxo-5-(2-furyl)-trans-1-penten-1-yl)-cyclopent-1α-yl]acetic Acid, γ-lactone (3C)

Dimethyl 2-oxo-4-(2-furyl) butylphosphonate (2C) (5.2 g, 21.1 mmole) was added to a mixture of 230 ml anhydrous DME and 57% NaH (860 mg, 20 mmole), and heated to reflux until no hydrogen was given off (1hour). After cooling, 5.2 g (21 mmole) 2-[3α-p-phenylbenzoyloxy-5α-hydroxy-2β-formylcyclopent-1α-yl]acetic acid, γ-lactone was added in one portion, followed by 100 ml DME. After 1 hour the reaction mixture was quenched with 2 ml glacial acetic acid, filtered and concentrated to dryness. The residue dissolved in ethyl acetate and was washed with 100 ml saturated sodium bicarbonate solution (4x), 100 ml water (2x), 100 ml saturated brine (1x), dried (MgSO₄) and evaporated to yield 6.02 g 2-[3α-p-phenylbenzoyloxy-5α-hydroxy-2β-(3-oxo-5-(2-furyl)-trans-1-penten-1-yl)cyclopent-1α-yl]acetic acid, γ-lactone (3C) as an oil after column chromatography (Silica gel, Baker, 60-200 mesh).

The ir spectrum (CHCl₃) of the product exhibited adsorbtion bands at 1774 cm⁻¹ (strong), 1710 cm⁻¹ (strong), 1670 cm⁻¹ (medium) and 1625 cm⁻¹ (medium)

attributable to the carbonyl groups and at 973 cm$^{-1}$ for the trans double bond.

The product of this example (3C) may be converted to 13,14-dihydro-17-(2-furyl)-ω-trisnorprostaglandins of the A, E or F series through the procedures of examples 10 12–13, and 15–18.

The product (3C) may also be converted to 15-lower alkyl-17-(2-furyl)-ω-trisnorprostaglandins of the A, E or F series by the procedures of examples 4–20.

15-lower alkyl-17-(2-furyl)-ω-tetranorprostaglandins of the A, E or F series may be obtained from (3C) via the procedures of examples 10–13 and 15–18. In a similar manner the 2-[3α-p-phenylbenzoyloxy-5α-hydroxy-2β-(3-oxo-3-(3-furyl-trans-1-propen-1-yl)-cyclopent-1α-yl]acetic acid, γ-lactone was prepared m.p. 140°–141° C. IR 1715, 1775, 1625, 1675, 975 cm$^{-1}$.

EXAMPLE 52

2-[3α-p-Phenylbenzoyloxy-5α-hydroxy-2β-(3α-hydroxy-5-(2-furyl)-trans-1-penten-1-yl)cyclopent-1α-yl]acetic acid, γ-lactone (4C) and
2-[3α-p-phenylbenzoyloxy-5α-hydroxy-2β-(3β-hydroxy-5-(2-furyl)-trans-1-penten-1-yl)cyclopent-1α-yl]acetic Acid, γ-lactone (5C).

To a solution of 5.97 g (12.7 mmole) 2-[3α-p-phenylbenzoyloxy-5α-hydroxy-2β-(3-oxo-5-(2-furyl)-trans-1-penten-1-yl) cyclopent-1α-yl]acetic acid, γ-lactone (3C)in 3ml dry 1,2-dimethoxyethane in a dry nitrogen atmosphere at ambient temperature was added dropwise 12.7 ml of a 0.5 M zinc borohydride solution. After stirring at room temperature for 45 minutes, a saturated sodium bitartrate solution was added dropwise until hydrogen evolution ceased. The reaction mixture was allowed to stir for 5 minutes, at which time 300 ml dry methylene chloride was added. After drying (MgSO$_4$) and concentrating (water aspirator), the resultant semi-solid was purified by column chromatography on silica gel (Baker "Analyzed" Reagent 60–200 mesh) using ether as eluent. After elution of less polar impurities, a fraction containing 2.26 g 2-[3α-p-phenylbenzoyloxy-5α-hydroxy-2β-(3α-hydroxy-5-(2-furyl)-trans-1-penten-1-yl)cyclopent-1α-yl]acetic acid, γ-lactone (4C), a 270 mg fraction of mixed 4C and 5C and finally a fraction (2.2 g) of 2-[3α-p-phenylbenzoyloxy-5α-hydroxy-2β-(3β-hydroxy-5-(2-furyl)-trans-1-penten-yl) cyclopent-1α-yl]acetic acid, γ-lactone (5C).

The ir spectrum (CHCl$_3$) of 4C and B 5C had strong carbonyl absorbtions at 1770 and 1710 cm$^{-1}$ and an absorbtion at 970 cm$^{-1}$ for the trans double bond.

EXAMPLE 53

2-[3α,5α-Dihydroxy-2β-(3α-hydroxy-5-(2-furyl)-trans-1-penten-1-yl)cyclopent-1α-yl]acetic acid, γ-lactone (6C)

A heterogeneous mixture of 2.26 g (4.8 mmole) of 2-[3α-p-phenylbenzoyloxy-5α-hydroxy-2β-(3α-hydroxy-5-(2-furyl)-trans-1-penten-1-yl)cyclopent-1α-yl]acetic acid, γ-lactone (4C), 26 ml. of absolute methanol and 660 mg of finely powdered, anhydrous potassium carbonate was stirred at room temperature for one hour, then cooled to 0°. To the cooled solution was added 9.6 ml of 1.0N aqueous hydrochloric acid. After stirring at 0° for an additional 10 minutes, 20 ml. of water was added with concomitant formation of methyl p-phenylbenzoate which was collected by filtration. The filtrate was saturated with solid sodium chloride, extracted with ethyl acetate (4 × 20 ml.), the combined organic extracts were washed with saturated sodium bicarbonate (10 ml.), dried (MgSO4) and concentrated to give 1.02 g of viscous, oily 2-[3α,5α-dihydroxy-2β-(3α-hydroxy-5-(2-furyl)-trans-1-penten-1-yl)cyclopent-1α-yl]acetic acid, γ-lactone (6C).

The ir spectrum (CHCl$_3$) exhibited a strong absorption at 1765 cm$^{-1}$ for the lactone carbonyl and medium absorption at 960 cm$^{-1}$ for the trans-double bond.

EXAMPLE 54

2-[5α-Hydroxy-3α-(tetrahydropyran-2-yloxy)-2β-(3α-{tetrahydropyran-2-yloxy}-5-(2-furyl)-trans-1-penten-1-yl)cyclopent-1α-yl]acetic acid, γ-lactone (7C)

To a solution of 1 gm (3.42 mmole) 2-[3α,5α-dihydroxy-2β-(3α-hydroxy-5-(2-furyl)-trans-1-penten-yl)cyclopent-1α-yl] acetic acid, γ-lactone (6C) in 5 ml anhydrous methylene chloride and 0.93 ml of 2,3-dihydropyran at 0° in a dry nitrogen atmosphere was added 10 mg p-toluenesulfonic acid, monohydrate. After stirring for 15 minutes, the reaction mixture was combined with 100 ml ether, the ether solution washed with saturated sodium bicarbonate (1 × 15 ml) then saturated brine (1 × 20 ml), dried (MgSO$_4$) and concentrated to yield 1.63 g (>100%) crude 2-[5α-hydroxy-3α-(tetrahydropyran-2-yloxy)-2β-(3α-{tetrahydropyran-2-yloxy}-5-(2-furyl)-trans-1-penten-1-yl)cyclopent-1α-yl]acetic acid, γ-lactone (7C).

The ir (CHCl$_3$) spectrum has a strong absorptions at 960 cm$^{-1}$. for trans double bond.

The product of this example (7C) may be converted to 13,14-dihydro-17-(2-furyl)-ω-trisnorprostaglandins of the A, E or F series through the procedures of examples 10, 12, 14–18.

EXAMPLE 55

2-[5α-Hydroxy-3α-(tetrahydropyran-2-yloxy)-2β-(3α-{tetrahydropyran-2-yloxy}-5-(2-furyl)-trans-1-penten-1-yl)cyclopent-1α-yl]acetaldehyde, γ-hemiacetal (8C)

A solution of 1.6 g (3.4 mmole) 2-[5α-hydroxy-3α-(tetrahydropyran-2-yloxy)-2β-(3α-tetrahydropyran-2-yloxy-5-(2-furyl)-trans-1-pentene-1-yl)cyclopent-1α-yl] acetic acid, γ-lactone (7C) in 16 ml dry toluene was cooled to −78° in a dry nitrogen atmosphere. To this cooled solution was added 4.68 ml of 0.8M diisobutylaluminum hydride in n-hexane (Alfa Inorganics) dropwise at such a rate so that the internal temperature never rose above −65° (15 minutes). After an additional 45 minutes of stirring at −78°, anhydrous methanol was added until gas evolution ceased and the reaction mixture was allowed to warm to room temperature. The reaction mixture was combined with 150 ml ether, washed with 50% sodium potassium tartrate solution (4 × 20 ml), dried (Na$_2$SO$_4$) and concentrated to a quantitative yield of oily 2-[5α-hydroxy-3α-(tetrahydropyran-2-yloxy)-2β-(3α-{tetrahydropyran-2-yloxy}-5-(2-furyl)-trans-1-penten-1-yl)cyclopent-1-yl]acetaldehyde, γ-hemiacetal (8C).

EXAMPLE 56

9α-Hydroxy-11α,15α-bis-(tetrahydropyran-2-yloxy)-17-(2-furyl)-cis-5-trans-13-ω-trisnor-prostadienoic Acid (9C)

To a solution of 3.36 g (7.6 mmole) (4-carbohydroxy-n-butyl) triphenylphosphonium bromide in a dry nitrogen atmosphere in 15.0 ml dry dimethyl sulfoxide was added 7.0 ml (14.0 mmole) of a 2.0M solution of sodium methylsufinylmethide in dimethyl sulfoxide. To this red ylide solution was added dropwise a solution of 1.3 g (2.81 mmole) 2-[5α-hydroxy-3α-(tetrahydropyran-2-yloxy)-2β-(3α-{tetrahydropyran-2-yloxy}-5-(2-furyl)-trans-1-penten-1-yl)cyclopent-1α-yl]acetaldehyde, γ-hemiacetal (8C) in 5.0 ml dry dimethyl sulfoxide over a period of 20 minutes. After an additional 2 hours stirring at room temperature, the reaction mixture was poured onto ice water. The basic aqueous solution was washed twice with ethyl acetate (20 ml.) and acidified to pH ~3 with 10% aqueous hydrochloric acid. The acidic solution was extracted with ethyl acetate (3 × 20 ml) and the combined organic extracts washed once with water (10 ml.), dried (MgSO$_4$) and evaporated to a solid residue. This solid residue was triturated with ethyl acetate and filtered. The filtrate was purified by column chromatography on silica gel (Baker "Analyzed" Reagent 60–200 mesh) using ethyl acetate as eluent. After removal of high R$_f$ impurities, 1.53 g of 9α-hydroxy-11α,15α-bis-(tetrahydropyran-2-yloxy)-17-(2-furyl)-cis-5-trans-13-ω-trisnor-prostadienoic acid (9C) was collected.

EXAMPLE 57

9-Oxo-11α,15α-bis-(tetrahydropyran-2-yloxy)-17-(2-furyl)-cis-5-trans-13-ω-trisnor-prostadienoic Acid (10C)

To a solution cooled to −10° under nitrogen of 1.1g (2.01 mmole)9α-hydroxy-11α,15α-bis-(tetrahydropyran-2-yloxy)-17-(2-furyl)-cis-5-trans-13-ω-trisnor-prostadienoic acid (9C) in 20 ml. reagent grade acetone was added dropwise to 0.88 ml (2.2 mmole) of Jones' reagent. After 20 minutes at −10°, 0.260 ml. 2-propanol was added and the reaction mixture was allowed to stir an additional 5 minutes at which time it was combined with 75 ml. ethyl acetate, washed with water (3 × 10 ml.), dried (MgSO$_4$) and concentrated to give 425 mg of 9-oxo-11α,15α-bis-(tetrahydropyran-2-yloxy)-17-(2-furyl)-cis-5-trans-13-ω-trisnor-prostadienoic acid (10C).

EXAMPLE 58

9-Oxo-11α,15α-dihydroxy-17-(2-furyl)-cis-5-trans-13-ω-trisnor-prostadienoic Acid (11C)

A solution of 425 mg (0.782 mmole) 9-oxo-11α,15α-bis-tetrahydropyran-2-yloxy)-17-(2-furyl)-cis-5-trans-13-ω-trisnor-prostadienoic acid (10C) in 3.0 ml. of a 65:35 mixture of glacial acetic acid:water was stirred under nitrogen at 25° for 18 hours, then was concentrated by rotary evaporation. The resultant crude oil was purified by column chromatography on silica gel (Mallinckrodt CC-4 100–200 mesh) using ethyl acetate as eluent. After elution of less polar impurities, the crystalline 9-oxo-11α,15α-dihydroxy-17-(2-furyl)-cis-5-trans-13-ω-trisnor-prostadienoic acid (11C) mp 98°–99° weighing 204 mg was collected.

The product of this example (11C) can be converted to 17-(2-furyl)-ω-trisnorprostaglandins-E$_1$, E$_0$, A$_2$, A$_1$ and A$_0$ via the procedures of examples 19, 20, and 12.

EXAMPLE 59

9α,11α,15α-Trihydroxy-17-(2-furyl)-cis-5-trans-13-ω-trisnorprostadienoic Acid (12C)

A solution of 700 mg. (0.334 mmole) 9α-hydroxy-11α,15α-bis-tetrahydropyran-2-yloxy)-17-(2-furyl)-cis-5-trans-13-ω-trisnorprostadienoic acid (9C) in 5 ml. of a 65:35 mixture of glacial acetic acid:water was stirred under nitrogen at 25° for 20 hours, then was concentrated by rotary evaporation. The resultant crude oil was purified by column chromatography on silica gel (Mallinckrodt CC-4 100–200 mesh) using ethyl acetate as eluent. After elution of less polar impurities, the oily 9α,11α,15α-trihydroxy-17-(2-furyl)-cis-5-trans-13-ω-trisnorprostadienoic acid (12C) weighing 108 mg. was collected.

The ir (CHCl$_3$) had a carbonyl absorbtion at 1710 cm$^{-1}$ and a trans double bond absorbtion at 965 cm$^{-1}$.

The product of this example (12C) can be converted to 17-(2-furyl)-ω-trisnorprostaglandins F$_{1α}$ and F$_{0α}$ via the procedures of examples 19 and 20.

What is claimed is:

1. A compound of the structure:

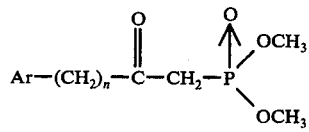

wherein Ar is α- or β-furyl and n is an integer from 1 to 5.

2. The compound of claim 1 wherein Ar is 2-furyl and n is 2.

* * * * *